(12) United States Patent
Kimura et al.

(10) Patent No.: US 8,114,098 B2
(45) Date of Patent: Feb. 14, 2012

(54) INSERTION APPARATUS FOR ENDOSCOPE

(75) Inventors: Koh Kimura, Hachioji (JP); Takayuki Suzuki, Yokohama (JP)

(73) Assignee: Olympus Corporation (JP)

( * ) Notice: Subject to any disclaimer, the term of this patent is extended or adjusted under 35 U.S.C. 154(b) by 1342 days.

(21) Appl. No.: 11/499,991

(22) Filed: Aug. 7, 2006

(65) Prior Publication Data

US 2006/0271066 A1 Nov. 30, 2006

Related U.S. Application Data

(63) Continuation of application No. PCT/JP2005/022011, filed on Nov. 30, 2005.

(30) Foreign Application Priority Data

Dec. 7, 2004 (JP) .................................. 2004-354617

(51) Int. Cl.
*A61B 17/10* (2006.01)

(52) U.S. Cl. .......................... 606/142; 606/143; 606/139
(58) Field of Classification Search .................. 606/142, 606/108, 167, 171, 177, 185, 213, 148, 144, 606/151, 139, 158
See application file for complete search history.

(56) References Cited

U.S. PATENT DOCUMENTS

| | | | |
|---|---|---|---|
| 2002/0045909 A1* | 4/2002 | Kimura et al. ................ | 606/151 |
| 2004/0243108 A1* | 12/2004 | Suzuki .............................. | 606/1 |

FOREIGN PATENT DOCUMENTS

| | | |
|---|---|---|
| JP | 62-164009 | 10/1987 |
| JP | 7-255734 | 10/1995 |
| JP | 8-280701 | 10/1996 |
| JP | 9-149905 | 6/1997 |
| JP | 11-197102 | 7/1999 |
| JP | 2001-120558 | 5/2001 |
| JP | 2002-191609 | 7/2002 |
| JP | 2004-261463 | 9/2004 |

OTHER PUBLICATIONS

Letter from Chinese Associate to Japanese Associate explaining enclosure of Chinese Office Action.
Untranslated Chinese Office Action issued Feb. 22, 2008 in connection with corresponding Chinese.
Application No. 200580004842.3 and English translation submitted in lieu of statement of relevancy.
International Preliminary Report on Patentability in corresponding PCT Appln. No. PCT/JP2005/022011 dated Jun. 21, 2007.
Japanese Office Action mailed Jun. 16, 2009 in corresponding Japanese Patent Application No. 2004-354617 (with English language translation).

* cited by examiner

*Primary Examiner* — Tuan Nguyen
(74) *Attorney, Agent, or Firm* — Ostrolenk Faber LLP

(57) ABSTRACT

An insertion apparatus for an endoscope comprises a tubular body which is inserted into a surgical tool insertion channel of the endoscope, and a wire member which is inserted into an inside cavity of the tubular body. The tubular body includes a distal end coil which is provided in the distal end side of the tubular body, a proximal end coil which is provided at the proximal end of the distal end coil, and has an inside diameter smaller than an inside diameter of the distal end coil, and an inside diameter changed member which is provided between the proximal end of the distal end coil and the distal end of the proximal end coil, and changed in the inside diameter to connect the proximal end of the distal end coil and the distal end of the proximal end coil.

14 Claims, 18 Drawing Sheets

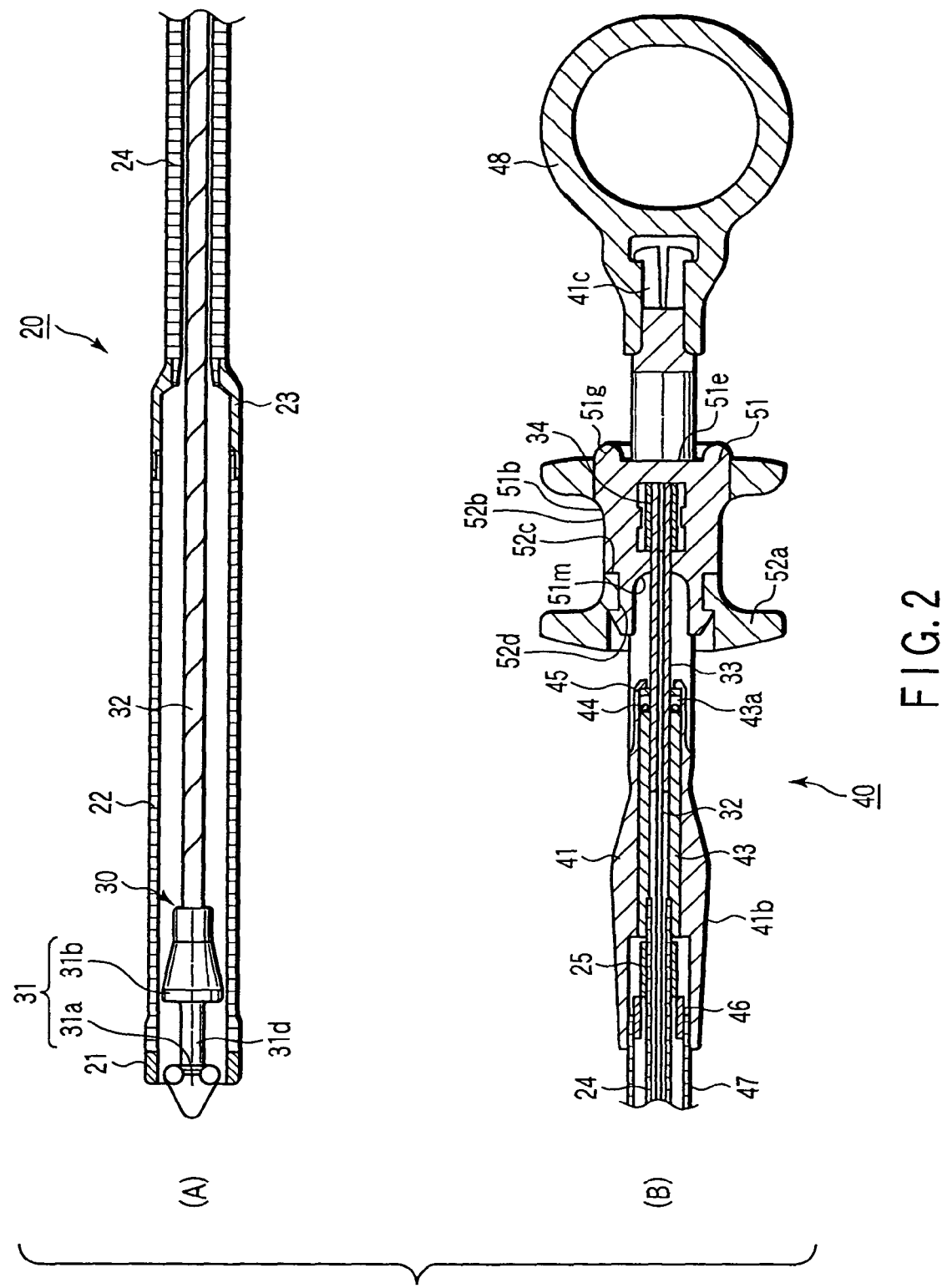
F I G. 2

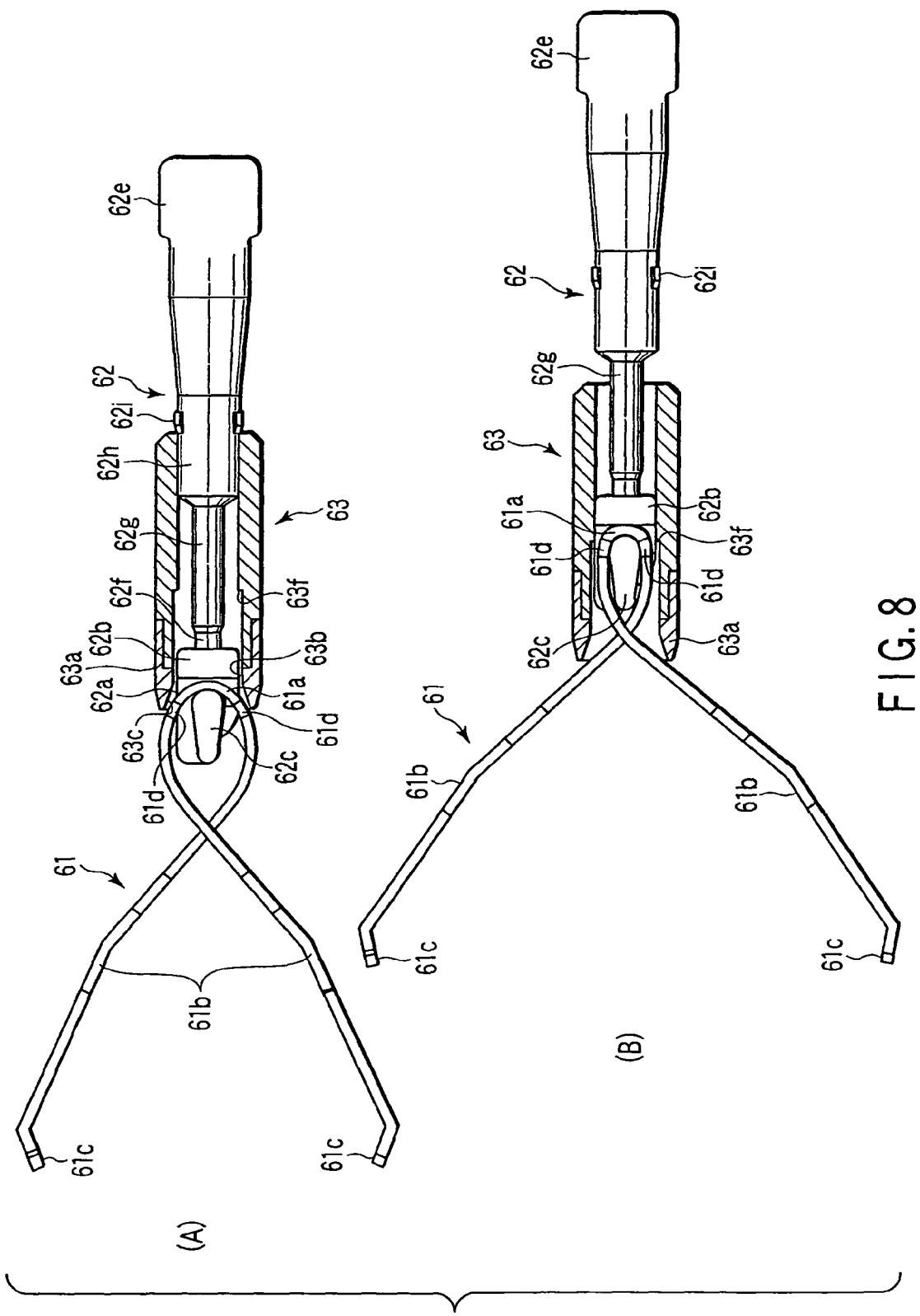
F I G. 8

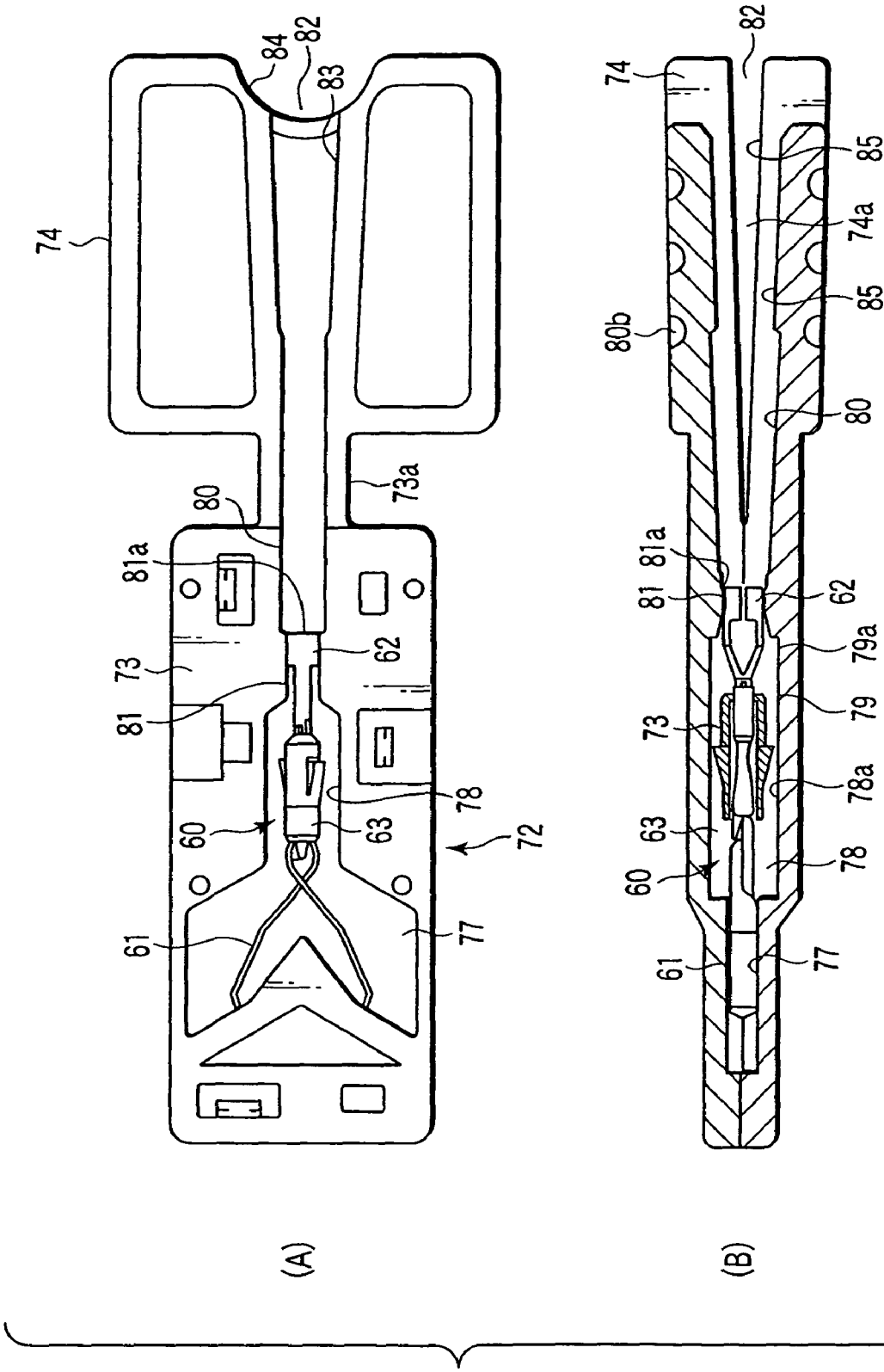
F I G. 10

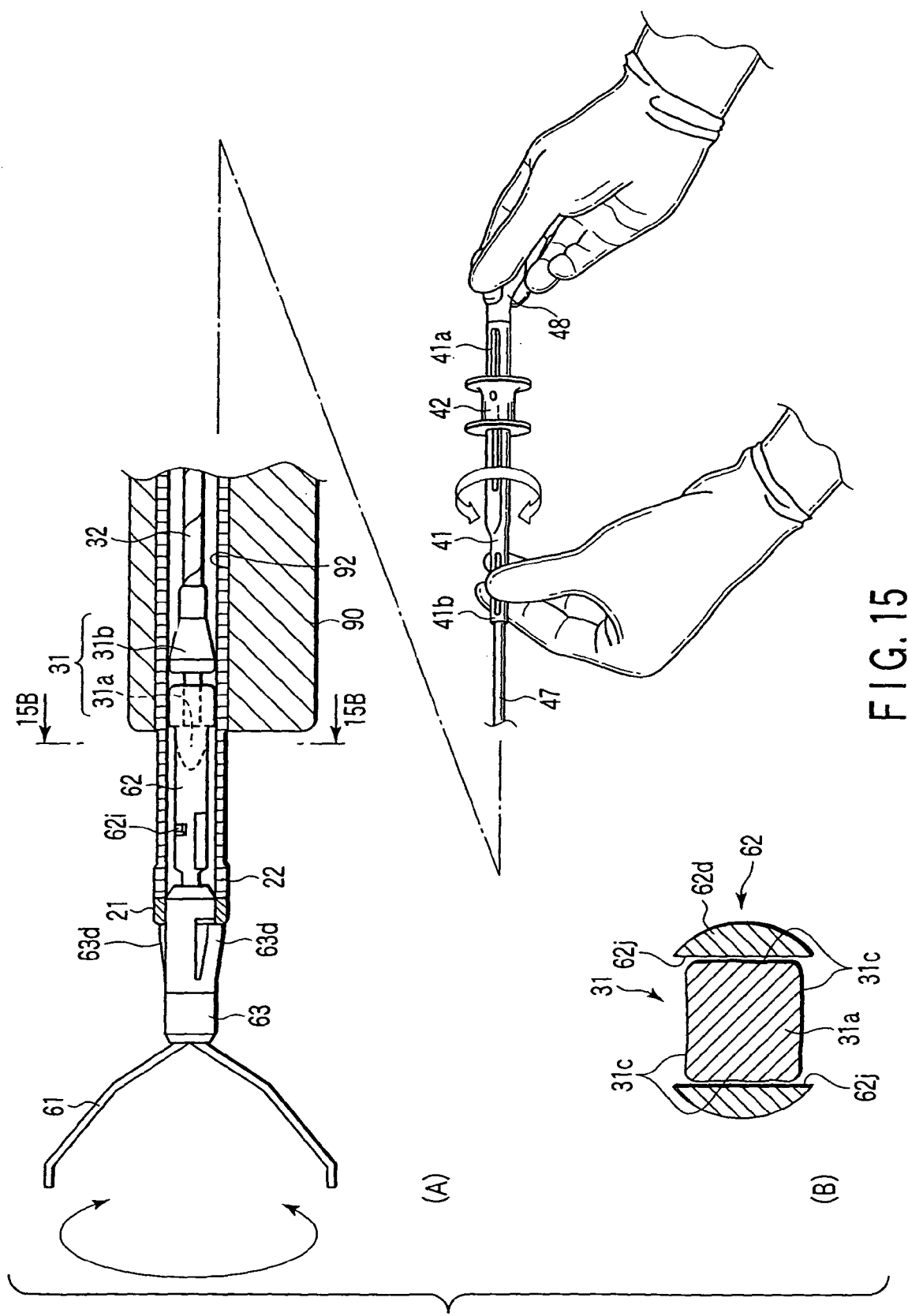
F I G. 15

INSERTION APPARATUS FOR ENDOSCOPE

CROSS-REFERENCE TO RELATED APPLICATIONS

This is a Continuation Application of PCT Application No. PCT/JP2005/022011, filed Nov. 30, 2005, which was published under PCT Article 21(2) in Japanese.

This application is based upon and claims the benefit of priority from prior Japanese Patent Application No. 2004-354617, filed Dec. 7, 2004, the entire contents of which are incorporated herein by reference.

BACKGROUND OF THE INVENTION

1. Field of the Invention

The present invention relates to an insertion apparatus used with an endoscope having a flexible insertion section, such as a biopsy forceps and a clip insertion apparatus.

2. Description of the Related Art

Jpn. Pat. Appln. KOKAI Publication No. 8-280701 discloses an insertion apparatus used with an endoscope having a flexible insertion section. An insertion apparatus, such as a biopsy forceps and a clip insertion apparatus, has an insertion portion including an outer tube (tubular member) 120 which is a metallic coil made of stainless steel for example, and a control wire 130 which is inserted into the outer tube 120 and made by a thin metallic single wire or twisted wire connected to a surgical tool at the distal end, as shown in FIG. 23 and FIG. 24. The control wire 130 includes a hook unit 131 to engage with a surgical tool such as a clip unit, and a wire 132. A cylindrical connection member 131b is provided between the hook unit 131 and wire 132. It is necessary to pull an operation member such as the control wire 130 with respect to the outer tube 120 by a strong force, in order to operate a surgical tool provided at or engaged with the end of the control wire 130.

To be formed along the curve of an insertion section of an endoscope or to have a structure easy to operate, it is common to form the outer tube 120 by connecting two coils 122 and 124 (refer to FIG. 23) in the distal end side and proximal end side, and to make the distal end coil 122 more flexible than the proximal end coil 124. In the outer tube 120, the proximal end of the distal end coil 122 and the distal end of the proximal end coil 124 thicker and smaller in diameter than the distal end coil 122 are directly connected by laser welding, for example. In addition to the above, the control wire 130 is generally formed by connecting two wires, to make the distal end side more flexible than the proximal end side.

The above configuration realizes the flexibility adaptable to the bending of a flexible endoscope, while providing the outer tube 120 bearable to a strong pulling force.

BRIEF SUMMARY OF THE INVENTION

According to an aspect of the invention, there is provided an insertion apparatus for an endoscope including a tubular member inserted into a surgical tool insertion channel of an endoscope, and a wire member inserted into the inside cavity of the tubular member. The tubular member includes a distal end coil which is provided in the distal end side of the tubular member, a proximal end coil which is provided at the proximal end of the distal end coil and has the inside diameter smaller than the inside diameter of the distal end coil, and an inside diameter changed member which is provided between the proximal end of the distal end coil and the distal end of the proximal end coil, and changed in the inside diameter to connect the proximal end of the distal end coil and the distal end of the proximal end coil.

BRIEF DESCRIPTION OF THE SEVERAL VIEWS OF THE DRAWING

FIG. 2 is a partially sectional view of the clip insertion apparatus according to the first embodiment;

FIG. 2(A) is a partially sectional schematic view of a distal end of the clip insertion apparatus;

FIG. 2(B) is a partially sectional schematic view of a proximal end of the clip insertion apparatus;

FIGS. 8(A) and 8(B) are partially sectional schematic views of the clip unit according to the first embodiment;

FIG. 10(A) is a schematic plane view showing the state that the clip unit is set in the cartridge according to the first embodiment;

FIG. 10(B) is a schematic sectional view showing the state that the clip unit is set in the cartridge according to the first embodiment;

FIG. 15(A) is a partially sectional schematic view showing rotation of the clip unit by rotating a rotary grip of the control unit body in the proximal end side of the clip insertion apparatus, in the state that the clip insertion apparatus provided with the clip unit according to the first embodiment is inserted into the surgical tool insertion channel of the insertion section of the endoscope, a retractable wing of the clip unit is provided at the distal end of the insertion tube, and the clip is pulled to the proximal end side of the insertion apparatus and opened to the maximum extent possible;

FIG. 15(B) is a schematic sectional view taken along lines 15B-15B of FIG. 15(A);

DETAILED DESCRIPTION OF THE INVENTION

Best mode for carrying out the invention will be explained hereinafter with reference to the accompanying drawings. A first embodiment will be explained with reference to FIG. 1 to FIG. 19.

Figure 6:
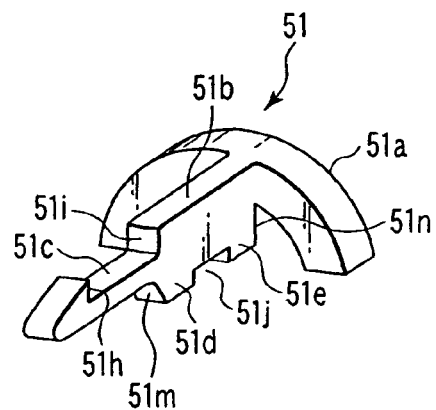
FIG. 6 is a schematic perspective view showing the structure of a first slide member of a slider of a control unit of the clip insertion apparatus according to the first embodiment.
Figure 7:
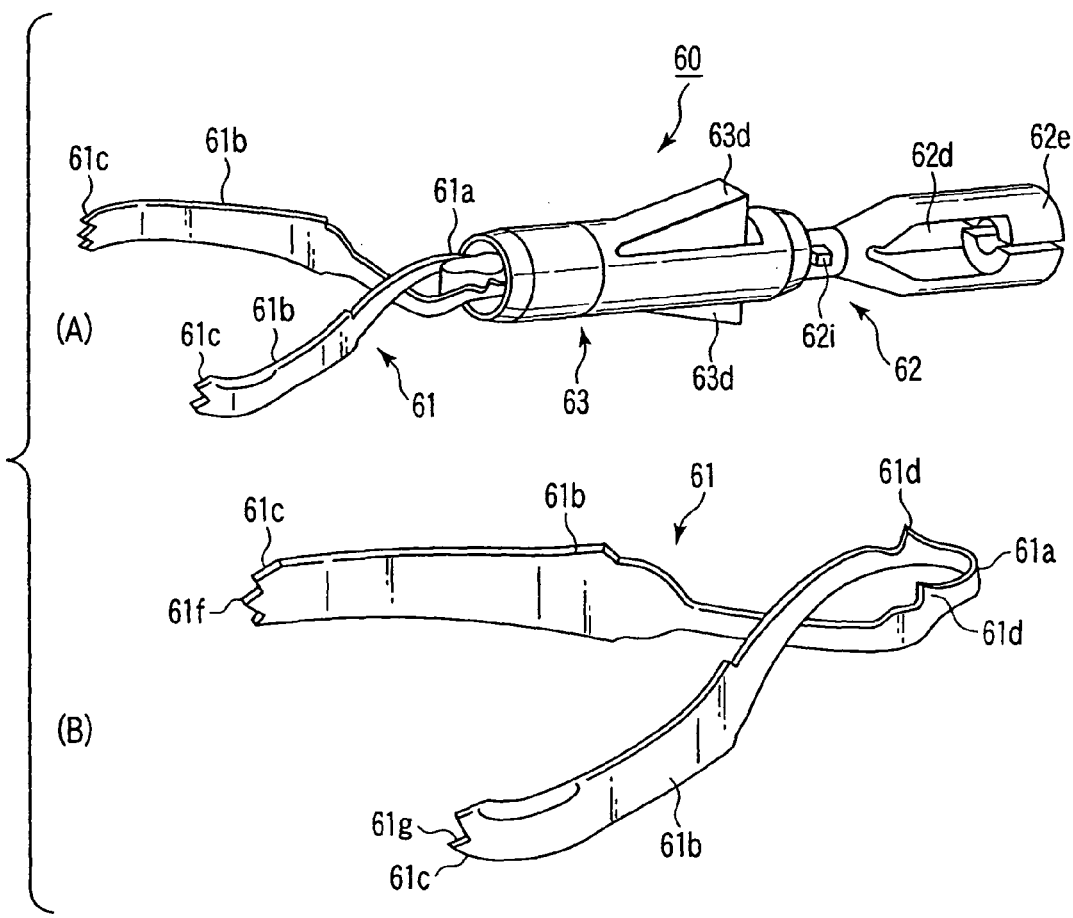
FIG. 7(A) is a schematic perspective view of a clip unit according to the first embodiment.
FIG. 7(B) is a schematic perspective view of a clip of the clip unit according to the first embodiment.
Figure 9:
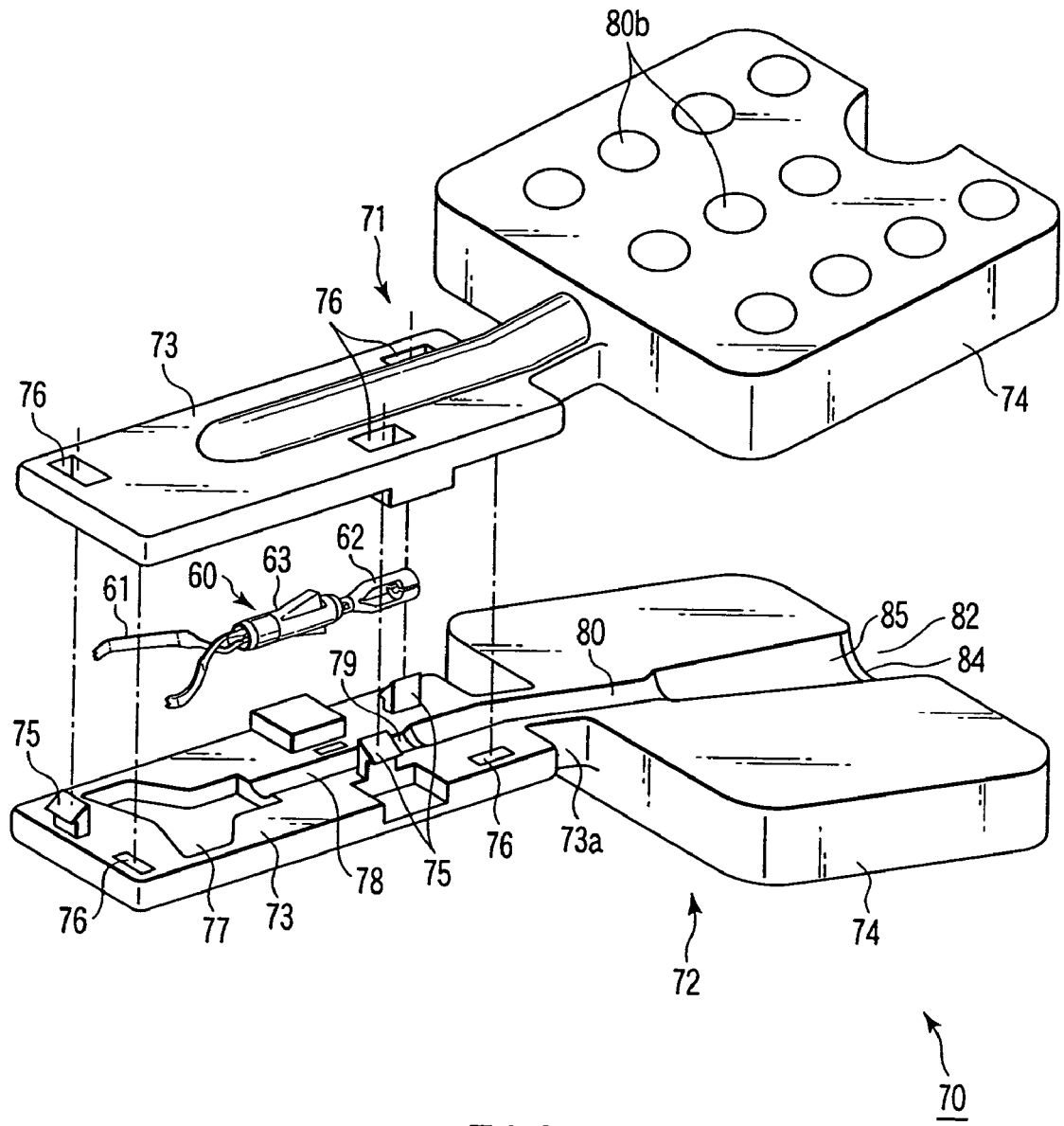
FIG. 9 is an exploded perspective view of a cartridge used to set the clip unit in the clip insertion apparatus according to the first embodiment.
Figure 13:
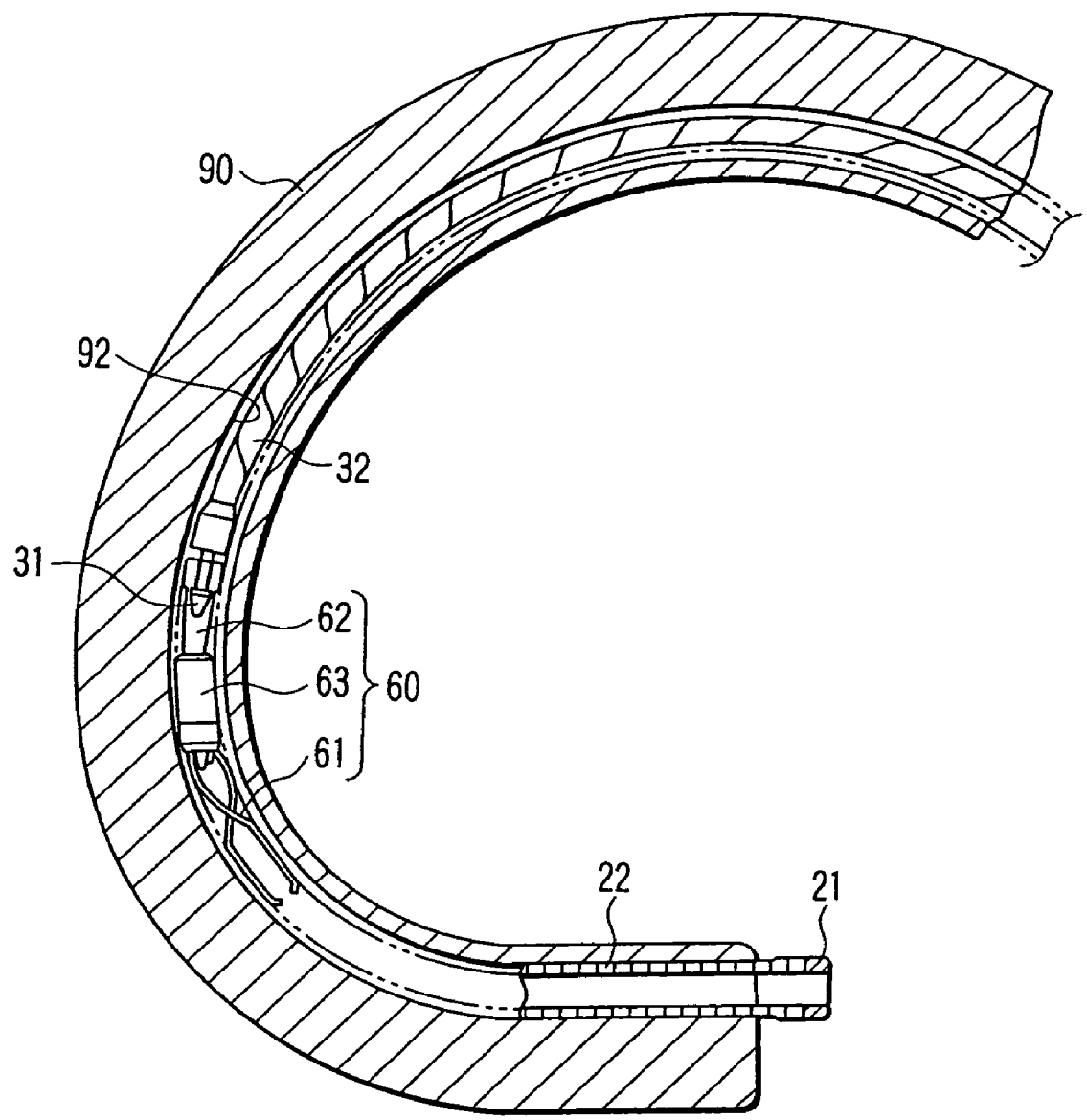
FIG. 13 is a schematic sectional view showing the state that the clip insertion apparatus provided with the clip unit according to the first embodiment is inserted into a surgical tool insertion channel of an insertion section of an endoscope, and the insertion section is bent.
Figure 14:
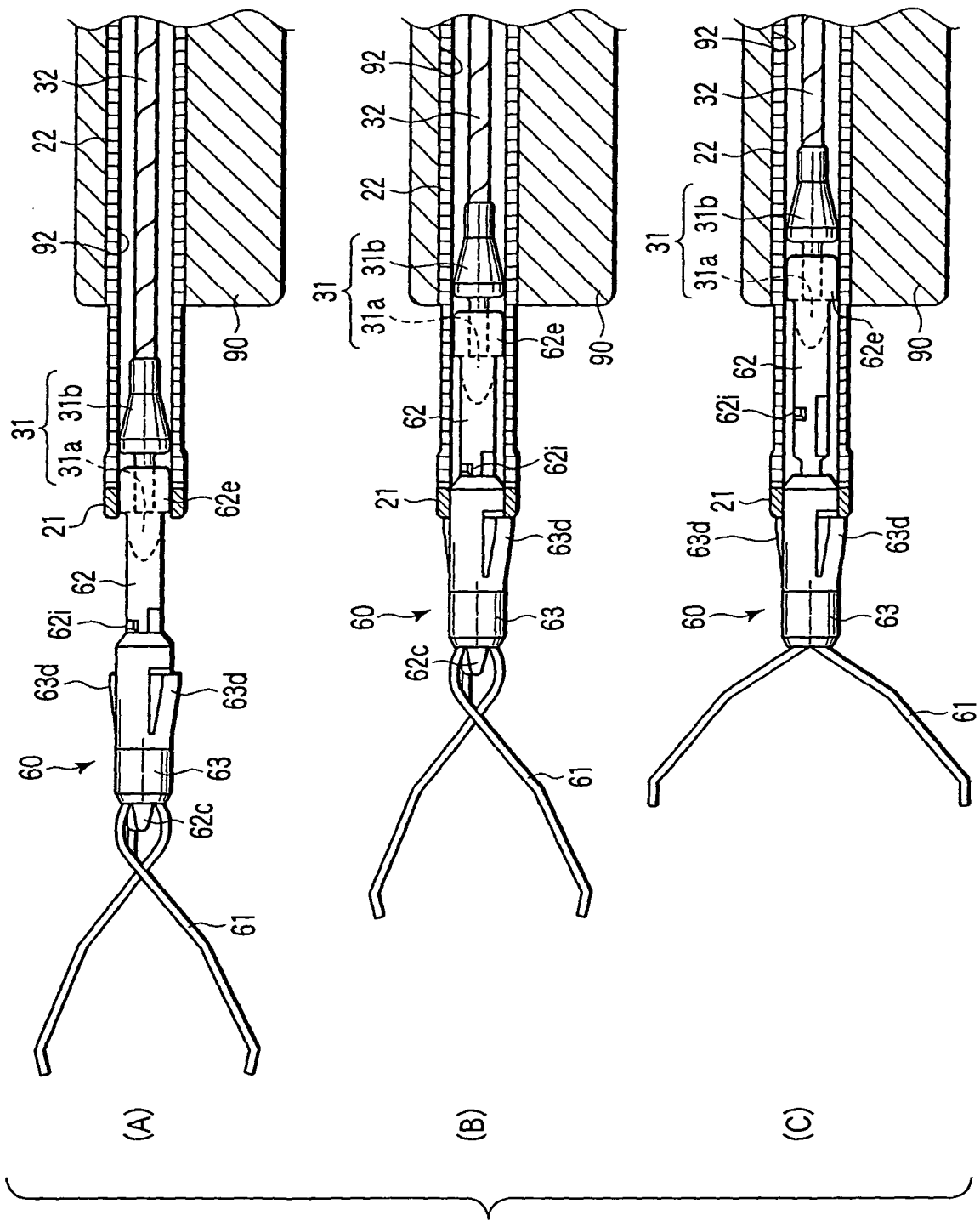
FIG. 14(A) is a partially sectional schematic view showing the clip unit projected from the distal end of the insertion section, in the state that the clip insertion apparatus provided with the clip unit according to the first embodiment is inserted into the surgical tool insertion channel of the insertion section of the endoscope.
FIG. 14(B) is a partially sectional schematic view showing a retractable wing of the clip unit engaged with the distal end of the insertion tube, in the state that the clip insertion apparatus provided with the clip unit according to the first embodiment is inserted into the surgical tool insertion channel of the insertion section of the endoscope.
FIG. 14(C) is a partially sectional schematic view showing the clip pulled to the proximal end side of the clip insertion apparatus and opened to the maximum extent possible, in the state that the clip insertion apparatus provided with the clip unit according to the first embodiment is inserted into the surgical tool insertion channel of the insertion section of the endoscope, and a retractable wing of the clip unit is engaged with the distal end of the insertion tube.
Figure 16:
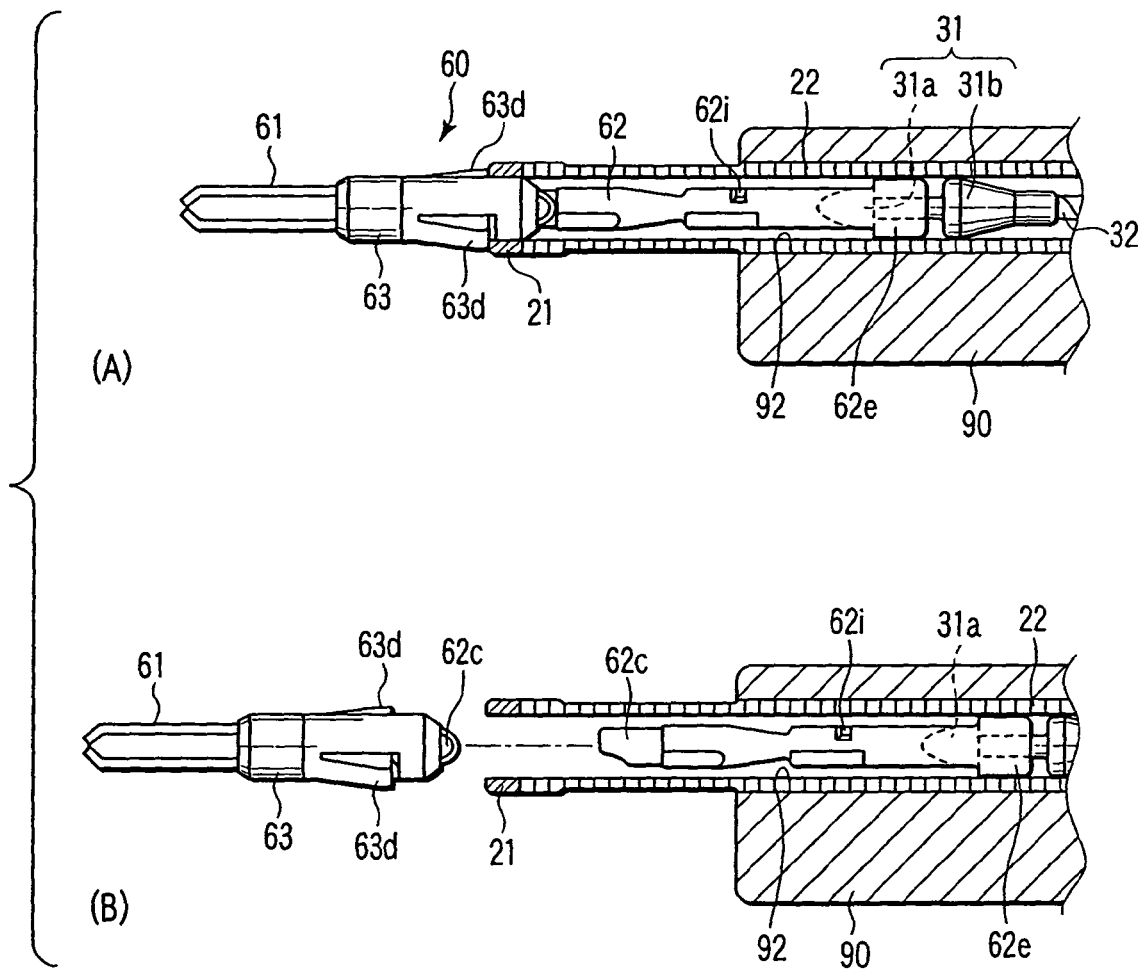
FIG. 16(A) is a partially sectional schematic view showing the clip pulled in the proximal end side of the clip insertion apparatus and closed, in the state that the clip insertion apparatus provided with the clip unit according to the first embodiment is inserted into the surgical tool insertion channel of the insertion section of the endoscope, and a retractable wing of the clip unit is engaged at the distal end of the insertion tube.
FIG. 16(B) is a partially sectional schematic view showing the clip pulled in the proximal end side of the clip insertion apparatus and the clip and ring of the clip unit are separated from a connection member, in the state that the clip insertion apparatus provided with the clip unit according to the first embodiment is inserted into the surgical tool insertion channel of the insertion section of the endoscope, and a retractable wing of the clip unit is engaged at the distal end of the insertion tube.

A surgical tool system for an endoscope according to the embodiment is used by combining a clip insertion apparatus 10 (refer to FIG. 1 to FIG. 6), a clip unit 60 (refer to FIG. 7(A) to FIG. 8), a cartridge 70 (refer to FIG. 9 to FIG. 10(B)), and an endoscope (refer to FIG. 13).

First, an explanation will be given on the structure of the clip insertion apparatus 10, which is a unit for inserting into an abdominal cavity (a control unit) according to the embodiment, with referent to FIG. 1 to FIG. 6.

Figure 1:
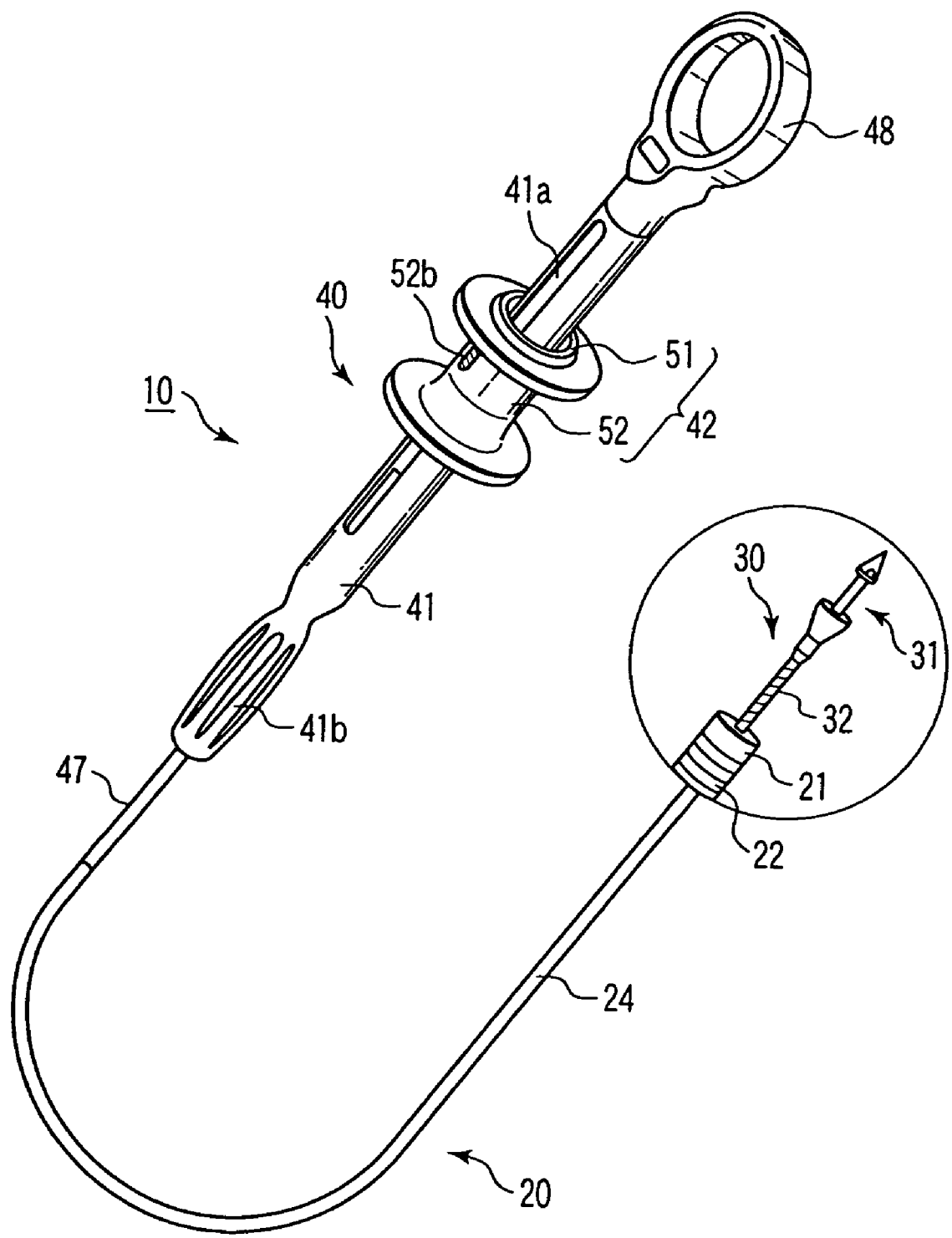
FIG. 1 is a schematic perspective view of a grip insertion apparatus according to a first embodiment of the invention.

As shown in FIG. 1, the clip insertion apparatus 10 includes an insertion tube 20, a control wire 30, and a control unit 40. The clip insertion apparatus 10 is used in combination with the endoscope, for example, by inserting into a surgical tool insertion channel (not shown) of the endoscope. Therefore, the insertion tube 20 is made sufficiently longer than the surgical tool insertion channel of the endoscope. The insertion tube 20 is given flexibility to be bent following the bending of the insertion section of the endoscope.

Figure 3:
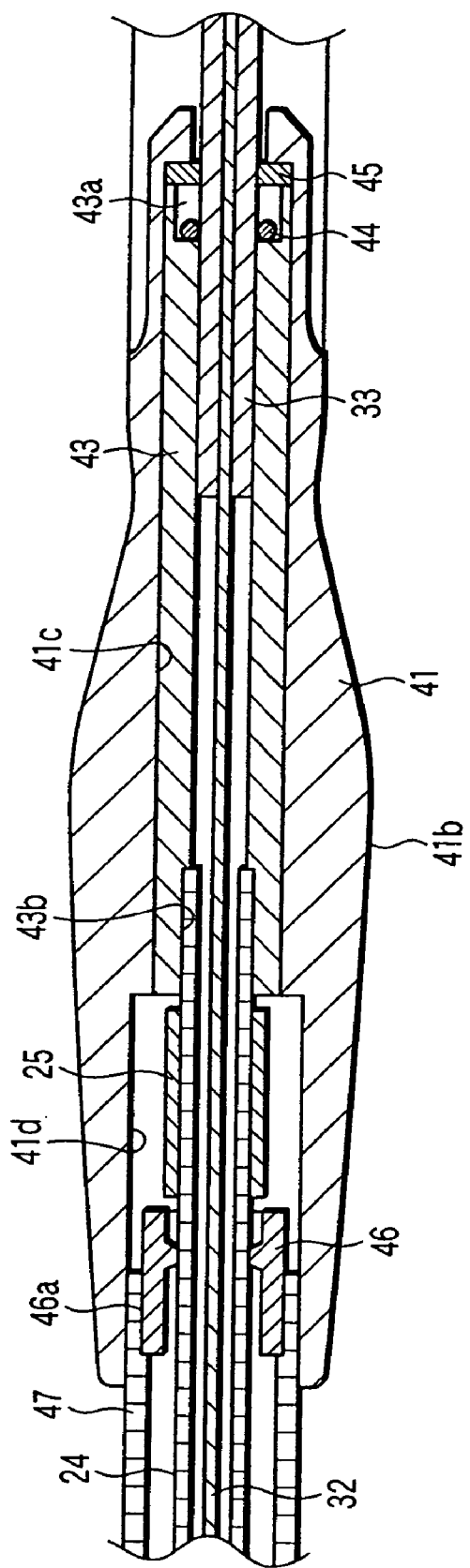
FIG. 3 is a schematic sectional view of a distal end of a control unit of the clip insertion apparatus according to the first embodiment.

As shown in FIG. 2(A), FIG. 2(B) and FIG. 3, the insertion tube 20 includes a distal end tip 21, a distal end coil 22, a coil connecting pipe 23, a proximal end coil 24, and a coil receiving pipe 25. The insertion tube 20 has a slender tubular shape.

As shown in FIG. 2(A), the distal end coil 22 is provided in the distal end side of the insertion tube 20. The distal end tip 21 is provided at the end of the distal end coil 22. The distal end tip 21 is made of stainless steel for example, and shaped annular with the inside diameter of 2 mm and outside diameter of 2-3 mm. The distal end of the insertion tube 20 that is one end of the distal end tip 21 is rounded smooth.

The distal end coil 22 is made by winding a stainless steel flat wire tightly, and shaped tubular. The coil 22 has the inside diameter of approximately 2 mm and outside diameter of 2.5-3 mm.

The coil connecting pipe 23 is provided at the proximal end of the distal end coil 22. The coil connecting pipe 23 is made of stainless steel for example, and shaped like a pipe having a short axial length. The proximal end of the distal end coil 22 and the distal end of the coil connecting pipe 23 are fixed by welding, for example. The inside diameter and outside diameter of the pipe 23 are gradually increased toward the distal end side. Namely, the inside diameter and outside diameter of the distal end of the pipe 23 are made larger than those of the proximal end. Therefore, the coil connecting pipe 23 has an arrowhead hook unit 31 described later of the control wire 30 in the distal end side, and prevents movement toward the proximal end side.

For example, the distal end of the coil connecting pipe 23 is formed to have the inside diameter of approximately 2 mm and outside diameter of 2.5-3 mm. The proximal end of the pipe 23 is formed to have the inside diameter of approximately 1 mm and outside diameter of 2-2.4 mm.

The proximal end coil 24 is provided at the proximal end of the coil connecting pipe 23. The coil 24 is made of stainless steel for example, and shaped like a cylinder. The proximal end of the coil connecting pipe 23 and the distal end of the proximal end coil 24 are fixed by welding, for example. The coil 24 is formed to have the inside diameter of approximately 1 mm and outside diameter of 2-2.4 mm.

As shown in FIG. 2(B) and FIG. 3, the coil receiving pipe 25 is fixed just like covering a part of the periphery of the proximal end of the proximal end coil 24. The coil receiving pipe 25 is made of stainless steel for example, and shaped like a pipe. The proximal end of the coil receiving pipe 25 is connected to the distal end of the control unit 40. The inside diameter of the pipe 25 is formed along the outside diameter of the proximal end coil 24, and the outside diameter of the pipe 25 is 2-4 mm.

As shown in FIGS. 2(A) and 2(B), the control wire 30 includes a hook unit 31, a wire 32, a control pipe 33, and a wire receiving pipe 34.

Figure 4:
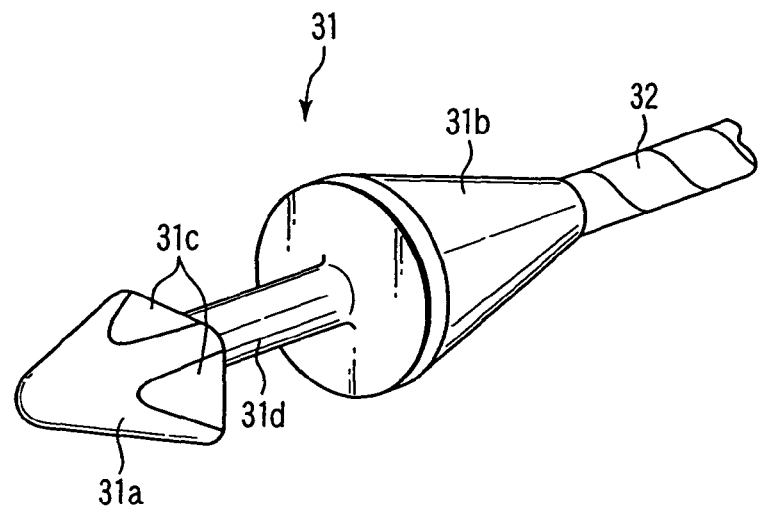
FIG. 4 is a schematic sectional view showing the structure of a distal end of a control wire of the clip insertion apparatus according to the first embodiment.
Figure 5:
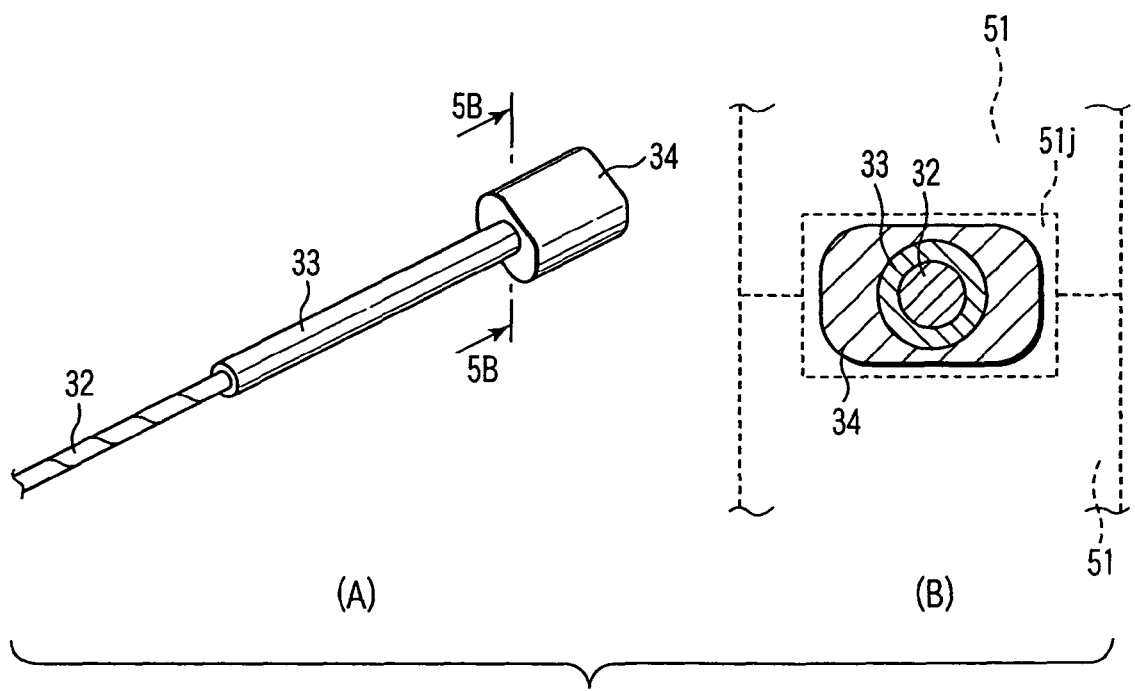
FIG. 5(A) is a schematic sectional view showing the structure of a proximal end of a control wire of the clip insertion apparatus according to the first embodiment.
FIG. 5(B) is a schematic sectional view taken along lines 5B-5B of FIG. 5(A)

The hook unit 31 is used to hook a clip unit 60 (refer to FIG. 7(A)). Namely, the hook unit 31 is used to connect the clip unit 60. As shown in FIG. 4, the hook unit 31 is formed to have a substantially conical distal end. The hook unit 31 is made of metal such as stainless steel. The hook unit 31 includes a conical engaging part 31*a* to hook and engage with the clip unit 60, and a wire connecting part 31*b* provided at the proximal end of the engaging part 31*a*. The wire connecting part 31*b* is formed substantially conical to reduce the diameter gradually from the distal end side to the proximal end side. Plane parts 31*c* are formed on the side of the proximal end on the cone of the engaging part 31*a*. Namely, the cross section of the distal end of the engaging part 31*a* is formed substantially circular, and the cross section of the proximal end is formed substantially rectangular (refer to FIG. 15(B)). Therefore, the engaging part 31*a* has a shape like an arrowhead. The proximal end of the clip unit engaging part 31*a* and the distal end of the wire connecting part 31*b* are connected with space by an axis 31*d* provided on the central axes of these parts.

The distal end of the wire 32 is fixed to the wire connecting part 31*b* by welding, for example. Namely the hook unit 31 is fixed to the distal end of the wire 32. The wire 32 is inserted retractably with respect to the insertion tube 20. The wire 32 is formed by twisting 19 solid wires made of metal such as stainless steel.

As shown in FIG. 3 and FIG. 5(A), the control pipe 33 is provided at the proximal end of the wire 32. The control pipe 33 is formed as a thin pipe (thickness of approximately 0.1 mm) made of metal such as stainless steel. The pipe 33 is swaged and fixed with the wire receiving pipe 34 at the proximal end of the wire 32. The pipe 33 is made longer than the moving stroke of a slider 42 described later, and provided just like covering the proximal end of the wire 32.

As shown in FIG. 2(B) and FIG. 5(A), the wire receiving pipe 34 is provided at the proximal end of the control pipe 33. The wire receiving pipe 34 is formed as a thick pipe made of metal. The pipe 34 is provided at the proximal end of the control pipe 33. As shown in FIG. 5(B), the pipe 34 is swaged with the control pipe 33 and fixed at the proximal end of the wire 32. The outer surface of the pipe 34 is formed flat by swaging.

As shown in FIG. 2(B) and FIG. 3, the control unit 40 includes a control unit main body 41, a slider 42, a guide pipe 43, an O-ring 44, a washer 45, a supporter mount 46, a supporter 47, and a thumb ring 48.

The main body 41 is formed by injection molding of resin. As shown in FIG. 1, the main body 41 includes a slit 41*a* to receive the slider 42, and a rotary grip 41*b* to rotate the whole main body 41 about the elongate axis. The rotary grip 41*b* is formed in the distal end side of the main body 41, and the slit 41*a* is formed in the proximal end side of the main body 41. The slit 41*a* is formed along the axial direction of the main body 41.

As shown in FIG. 2(B), a fitting part 41*c* to fit the thumb ring 48 is formed at the proximal end of the main body 41. Therefore, the thumb ring 48 is fit to the fitting part 41*c* movably about the axis.

As shown in FIG. 3, the central axis of the main body 41 has a hole 41*d* which has several steps and has the inside diameter larger at the distal end and smaller at the proximal end. The hole 41*d* is closed at the proximal end of the main body 41 (refer to FIG. 1 and FIG. 2(B)). The proximal end of the proximal end coil 24 is formed at the distal end of the hole 41*d* of the main body 41. On the outer surface of the proximal end of the proximal end coil 24, the supporter mount 46 is provided at the distal end of the coil receiving pipe 25. The supporter 47 is provided on the outer surface of the supporter mount 46. The outer surface of the proximal end of the supporter 47 is fixed to the distal end of the hole 41*d* of the main body 41.

The guide pipe 43 is provided in the hole 41*d* of the main body 41. Namely, the guide pipe 43 is fit to the inner surface of the main body 41. The guide pipe 43 is made of a metal such as stainless steel.

The guide pipe 43 includes an O-ring housing 43*a* to contain the O-ring 44, and a coil insertion part 43*b* to insert the proximal end of the proximal end coil 24. The O-ring 44 is provided in the O-ring housing 43*a*, and has an inside diameter much smaller than the outside diameter of the control pipe 33. Therefore, the internal circumference of the O-ring 44 is closely adhered to the outer surface of the control pipe 33.

The O-ring housing 43*a* is formed at the proximal end of the guide pipe 43. The O-ring housing 43*a* is caved from the inner surface toward the outside of the guide pipe 43. The O-ring housing 43*a* has an inside surface having an inside diameter larger than the outside diameter of the O-ring 44 and smaller than the outside diameter of the guide pipe 43. In the O-ring housing 43*a*, the O-ring 44 is provided in the length movable to the guide pipe 43 in a range of 2 to 6 mm, for example.

The washer 45 is provided just like covering the O-ring housing 43*a* from the proximal end side at the proximal end of the guide pipe 43. The washer 45 is made of metal having an inside diameter slightly larger than the outside diameter of the control pipe 33, and the outside diameter substantially the same as the guide pipe 43. Therefore, the O-ring 44 is movable while closely contacting the outer surface of the control pipe 33 in a range between the state contacting the washer 45 and the state isolated from the washer 45 and contacting the distal end of the O-ring housing 43*a*.

The slider 42 includes a first slide member 51 as a wire receiving holder, and a second slide member 52 engaged with the first slide member 51.

The first slide member 51 is provided as a pair to fix the wire receiving pipe 34 (refer to FIGS. 5(A) and 5(B)) provided at the proximal end of the wire 32. As shown in FIG. 6, the first slide member 51 includes a semi-ring 51a, an exposed part 51b, an engaging part 51c, and feet 51d and 51e. The slide member 51 is formed by injection molding of resin colored green, for example.

The semi-ring 51a is shaped like a half-doughnut, and engages with the proximal end of the second slide member 52. The semi-ring 51a is provided around the proximal end of the main body 41. A projection 51g is formed at the proximal end of the semi-ring 51a. The exposed part 51b is extended from the semi-ring 51a to the distal end side. The exposed part 51b is exposed on the outer surface in order to rest a finger when fitting with the second slide member 52. The engaging part 51c is extended to the distal end side at the distal end of the exposed part 51b. At the distal end of the engaging part 51c, a hook 51h to engage with the second slide member 52 is extended outward. Therefore, the hook 51h engages with the second slide member 52. The hook 51h receives the second slide member 52, when moving the slider 42 to the distal end side with respect to the slit 41a. Namely, a force is applied to the hook 51h, when moving the slider 42 to the distal end side.

Between the exposed part 51b and engaging part 51c, a receiving part 51i is formed to receive the force from the second slide member 52. Therefore, the receiving part 51i receives the second slide member 52, when moving the slider 42 to the proximal end side with respect to the slit 41a. The feet 51d and 51e are extended from the exposed part 51b toward the slit 41a of the main body 41. The feet 51d and 51e are slidable with respect to the slit 41a. Between the feet 51d and 51e, a fixing part 51j is formed to hold and fix the wire receiving pipe 34. As the wire receiving pipe 34 is fixed by the fixing part 51j, the wire receiving pipe 34 is also moved when the feet 51d and 51e are moved.

On the distal end surface of the foot 51d of the distal end side with respect to the main body 41, a slit applying surface 51m is formed to be applied to the distal end of the slit 41a of the main body 41. On the proximal end surface of the foot 51e of the proximal end side with respect to the main body 41, a slit applying plane 51n is formed to be applied to the proximal end of the slit 41a. These slit applying surfaces 51m and 51n control the moving amount of the slider 42 with respect to the slit 41a.

The second slide member 52 includes a finger rest 52a, a slit 52b, a slit end 52c, and a step 52d. The finger rest 52a is shaped like a pair of disks parallel to each other. Between the finger rest 52a of the distal end side and the finger rest 52a of the proximal end side, a slit 52b is formed to fit with the exposed part 51b. Therefore, the exposed part 51b of the first slide member 51 and the slit 52b of the second slide member 52 are engaged, and the outer surfaces of the second slide member 52 and exposed part 51b are formed to the same level. The slit 52b is fitted with the feet 51d and 51e of the first slide member 51. The slit end 52c of the distal end side of the slit 52b is brought into contact with the receiving part 51i at the proximal end of the engaging part 51c of the first slide member 51.

A step 52d is formed in the distal end side farther than the slit end 52c. The step 52d is brought into contact with the hook 51h of the distal end of the engaging part 51 of the first slide member 51. Therefore, the slider 42 engaged with the first slide member 51 and second slide member 52 is slidable with respect to the slit 41a of the main body 41.

The supporter mount 46 is provided at the distal end of the hole 41d of the main body 41. The supporter mount 46 has the inside diameter larger than the outside diameter of the proximal end coil 24 and smaller than the outside diameter of the coil receiving pipe 25. The outer surface of the distal end side of the supporter mount 46 has a screw 46a to permit insertion and screwing-on of the supporter 47.

The supporter 47 is made of coiled stainless steel solid wire. The supporter 47 is loose in the distal end side and tight in the proximal end side. The inner surface of the proximal end of the supporter 47 is engaged with the screw 46a of the supporter mount 46. At this time, the outer surface of the supporter 47 is tightly stuck to the inner surface of the distal end of the main body 41.

An explanation will now be given on the structure of the clip unit 60 as a surgical tool according to the embodiment with reference to FIG. 7(A) to FIG. 8(B).

The clip unit 60 can be fit to the hook unit 31 at the distal end of the wire 32 of the clip insertion apparatus 10. As shown in FIG. 7(A), the clip unit 60 includes a clip 61, a connection member 62, and a constraining pipe 63 as a tightening member.

As shown in FIG. 7(B), the clip 61 has a loop (base) 61a made by bending a metallic plate material such as a flat spring made of stainless steel, for example, at substantially a central part. The clip 61 is crossed in vicinity of the loop 61a, and extended as a pair of arms (clip arms) 61b having an expanding characteristic in the state that the distal ends are separated. A tissue grasping part (a clip claw) 61c is formed at the end of the clip 61.

The crossing part of the arms 61b of the clip 61 is made narrower than the distal end side, and the tissue grasping parts 61c are opposed to each other. In the vicinity of the loop 61a of the arm 61b, a sawtooth-shaped projection 61d projecting to the plate width direction is formed. As shown in FIG. 7(B), the projection 61d is formed sharp in the side of the tissue grasping part 61c and gentle in the side of the loop 61a. Therefore, the clip 61 slides on the inner surface of the constraining pipe 63 when moving the clip 61 in the direction of pulling into the pipe 63, but the clip 61 is engaged in the inner surface of the pipe 63 when moving the clip 61 in the direction reverse to the pulling-in direction.

The tissue grasping parts 61c are bent inward to an angle of 90-150° at the distal end of the arm 61b. One of the tissue grasping parts 61c has a substantially triangular convex 61f, and the other has a substantially triangular concave 61g to engage with the convex 61f.

The connection member 62 is formed by injection molding out of strong resin such, as liquid crystal polymer and polyamide synthetic fiber, for example. As shown in FIGS. 8(A) and 8(B), the connection member 62 is a cylindrical bar having a projection 62a at the distal end. The base 62b of the projection 62a is shaped substantially circular. In the distal end side of the projection 62a, a long flat elliptical projection 62c is formed in the axial direction. The loop 61a of the clip 61 is hung on the projection 62c, and the clip 61 is engaged with the connection member 62.

The other end of the connection member 62 is forked into two branches, and has a cutout 62d (refer to FIG. 7(A)). In the cutout 62d, a flat part 62j (refer to FIG. 15(B)) and an elastic arm 62e are formed. The flat part 62j comes into contact with the clip unit engaging part 31a at the end of the arrowhead hook unit 31 (refer to FIG. 14). The middle part of the connection member 62 has a thin-diameter portion 62f as a broken part, a middle-diameter portion 62g and a thick-diameter portion 62h, from the front end side to the rear end side. Particularly, the dimension of the thin-diameter portion 62f is set to break when a breaking force of 20-60 N is applied. The outside diameter of the thick-diameter portion 62h is set to engage tightly with the inner surface of the constraining pipe 63. The thick-diameter portion has a stopper projection 62i at a part of the outer surface.

The constraining pipe 63 is formed by injection molding of rigid resin having appropriate elasticity, such as a material more flexible than the clip 61, for example, polyphthalamide (PPA) and polyamide (PA). By fitting the pipe 63 to the arms 61b of the clip 61, the arms 61b of the clip 61 are closed.

A distal end pipe 63a made of rigid metal such as stainless steel is fitted to the distal end of the constraining pipe 63. The outside diameter of the distal end pipe 63a is the same as the outside diameter of the pipe 63, and the inside diameter is formed in an inside diameter slope 63c becoming gradually large from a minimum inside diameter portion 63d at the proximal end to the distal end. In the outer periphery of the constraining pipe 63, a pair of wings 63d (refer to FIG. 7(A)) elastically retractable in the radial direction is formed.

Next, an explanation will be given on the assembly work of the clip unit 60, combining the clip 61, connection member 62 and pipe 63.

As shown in FIG. 8(A), insert the connection member 62 from the proximal end side of the pipe 63, and project the projection 62c of the connection member 62 from the distal end pipe 63a of the pipe 63. In this state, hang the loop 61a of the clip 61 on the projection 62c. The clip 61 is engaged with the connection member 62.

Then, pull the connection member 62 toward the proximal end side. The loop 61a of the clip 61 is brought into contact with the inner surface of the distal end pipe 63a of the pipe 63. At this time, the stopper projection 62i of the connection member 62 is engaged with the end-face of the rear end side of the pipe 63, and the clip 61, connection member 62 and pipe 63 are engaged. This completes the assembly as shown in FIG. 8(A).

When the connection member 62 is pulled to the proximal end side in this state, the loop 61a of the clip 61 is pulled into the pipe 63 from the distal end pipe 63a of the pipe 63. Therefore, the loop 61a of the clip 61 is pressed, and the arms 61b are opened.

Then, pull the connection member 62 further to the proximal end side, as shown in FIG. 8(B). Though not shown in the drawing, the projection 61d of the clip 61 contacts the inside step 63f of the pipe 63. Therefore, the pulling the clip 61 into the pipe 63 is stopped, and the arms 61b are kept opening maximum.

When the connection member 62 is pulled further to the proximal end side in this state, the projection 61d of the clip 61 rides over the inside step 63f of the pipe 63, the clip 61 is pulled into the pipe 63, and the arms 61b of the clip 61 are closed.

As the pipe 63 is made of resin with an appropriate elasticity more flexible than the clip 61, the projection 61d of the clip 61 is engaged and locked in the inside wall of the pipe 63, the clip 61 is prevented from moving in the axial direction within the pipe 63. Therefore, the arms are kept closed. The projection 61d of the clip 61 is shaped like a sawtooth projecting in the plate width direction of the loop 61a. Therefore, the clip 61 is moved lightly to the tightening side (in the direction of closing the arms 61b), but prevented from moving to the returning side (in the direction of opening the arms 61b), because the projection 61d is engaged in the inside wall of the pipe 63.

The clip unit 60 is contained in the cartridge (clip case) 70, which facilitates insertion of the clip unit 60 into the clip insertion apparatus 10, as shown in FIG. 9 to FIG. 10(B). Therefore, an explanation will now be given on the structure of the cartridge 70 as a surgical tool according to the embodiment with reference to FIG. 9 and FIG. 10(B).

As shown in FIG. 9, the cartridge 70 containing the clip unit 60 includes an upper case 71 and a lower case 72, which have the same shape. The upper case 71 and lower case 72 are formed by injection molding of transparent resin with an appropriate rigidity, such as ABS, PC, PP, PS, acrylic, and cycloolefinpolymer. The cartridge 70 is formed to be easy to hold, with a width of 10-20 mm, length of 50 mm, and thickness of 5 mm.

A clip unit housing 73 is provided at one end of the longish side of the upper case 71 and lower case 72. A compression unit 74 is provided at the other end. The compression unit 74 is a 20×20 mm square easy to hold with the fingers, for example.

As shown in FIG. 10(B), the compression units 74 of the upper and lower cases 71 and 72 are bent to separate each other at a connection part 73a connecting the clip unit housing 73 and compression unit 74. Therefore, a clearance 74a is formed between the compression units 74.

As shown in FIG. 9, three engaging claws 75 and three engaging holes 76 are provided on the internal surfaces of the clip unit housing 73 in the upper and lower cases 71 and 72. The engaging claw 75 of the upper case 71 engages with the engaging hole 76 of the lower case 72, and the engaging claw 75 of the lower case 72 engages with the engaging hole 76 of the upper case 71. Therefore, the upper case 71 and lower case 72 are engaged.

The upper case 71 and lower case 72 have the same shape, and one of the cases, the lower case 72, will be explained.

As shown in FIG. 10(A), on the inner surface of the clip unit housing 73, a clip housing 77 consisting of substantially T-shaped and Y-shaped concaves is formed to contain the clip 61 of the clip unit 60 in the opened state. The clip housing 77 is continued to a pipe housing 78 and a connection member housing 79, which are formed as arc-shaped grooves. At the bottom of the pipe housing 78, a retractable wing housing concave 78a (refer to FIG. 10(B)) is formed to contain the retractable wing 63d of the clip unit 60. At the bottom of the connection member housing 79, an expanded part 79a of an elastic arm (refer to FIG. 10(B)) is provided to permit the elastic arm 62e to become deformed when engaging with the arrowhead hook unit 31.

On the inner surface of the compression unit 74, an insertion tube inserting part 80 formed as an arc-shaped groove is formed continuously from the connection member housing 79. On the outer surface of the compression unit 74, a plurality of hemisphere concaves 80b is formed as a slip stopper.

In the boundary between the connection member housing 79 and insertion tube inserting part 80, a distal end tip abutment 81a (refer to FIG. 10(B)) and a retractable wing diameter reducing part 81 with a slope of 5 to 90° are formed. When the pipe 63 of the clip unit 60 is passed through the retractable wing diameter reducing part 81, the retractable wing 63d is pressed to the inside.

The insertion tube inserting part 80 to insert the insertion tube 20 of the clip insertion apparatus 10 has a slop 83 gradually increased in diameter toward an inlet 82 (refer to FIG. 10(B)). The diameter of the inlet 82 is larger than 3 mm for example, and formed to have a semicircular arc-shaped surface 84 when viewed on a plane. At the bottom of the insertion tube inserting part 80, a projection is formed in length of 1-5 mm for example. An insertion tube fixing part 85 (refer to FIG. 10(B)) is formed to fix the insertion tube 20 by pressing vertically by the projection.

An explanation will now be given on the effects when using the clip insertion apparatus 10 of the embodiment by combining with the clip unit 60 and cartridge 70, with reference to FIG. 11 to FIG. 19.

Move the slider 42 of the clip insertion apparatus 10 shown in FIG. 1 and FIG. 2(B) until abutting against the proximal end side close to the thumb ring 48. At this time, the distal end of the hook unit 31 shown in FIG. 2(A) is placed at the position close to the coil connecting pipe 23, inside the distal end coil 22 of the insertion tube 20.

As shown in FIG. 10(A), the clip unit 60 is placed between the upper case 71 and lower case 72 of the cartridge 70. The clip 61 is set in the clip housing 77, the constraining pipe 63 is set in the pipe housing 78, and the connection member 62 is set in the connection member housing 79.

Figure 11:
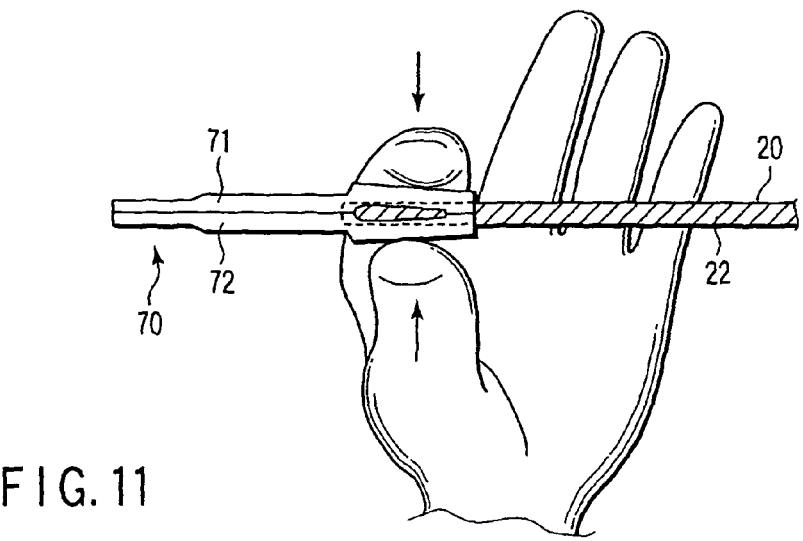
FIG. 11 is a view showing the state that an insertion tube of the clip insertion apparatus according to the first embodiment is inserted into and fixed to the cartridge provided with a clip unit.
Figure 12:
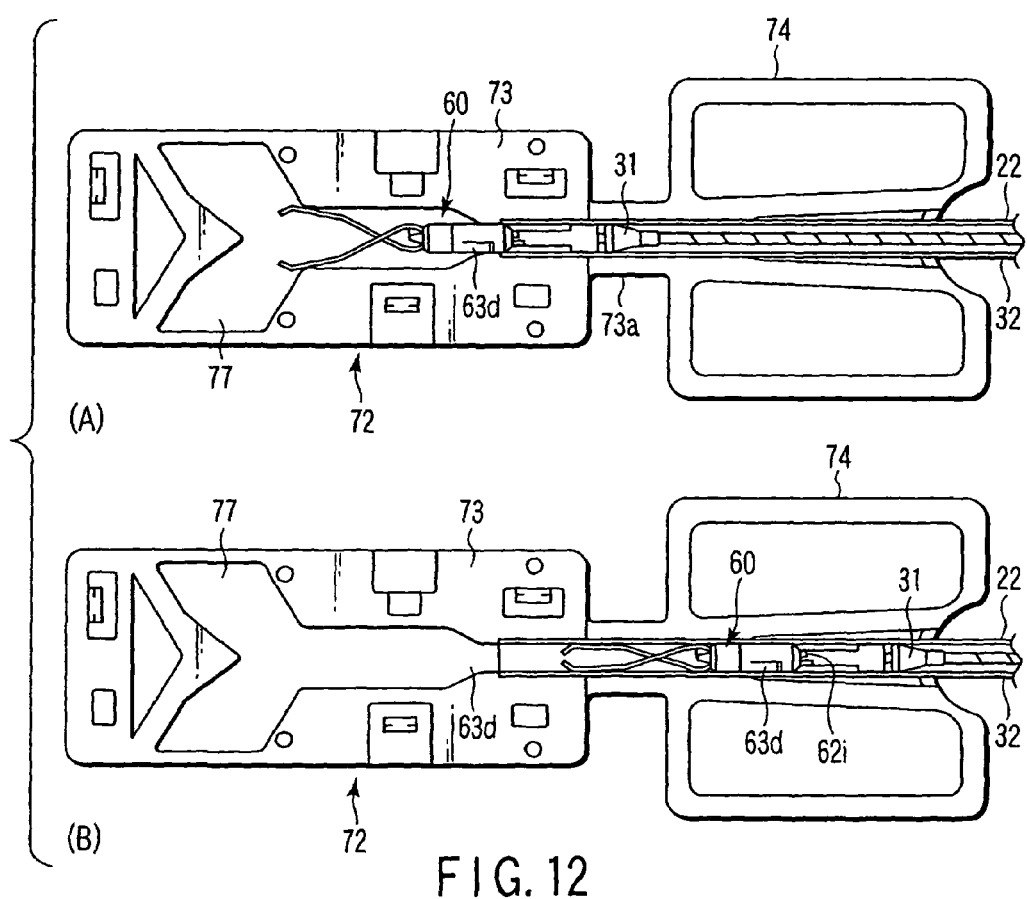
FIG. 12(A) is a schematic plane view showing the insertion tube removed from the cartridge in the state that the clip insertion apparatus and clip unit according to the first embodiment are engaged.
FIG. 12(B) is a schematic plane view showing the clip unit pulled into the insertion tube in the state that the clip insertion apparatus and clip unit according to the first embodiment are engaged.

Insert the insertion tube 20 of the clip insertion apparatus 10 from the inlet 82 of the cartridge 70 in the state shown in FIG. 10(B), deeply into the insertion tube inserting part (coil inserting part) 80, as shown in FIG. 11. Abut the distal end tip 21 of the insertion tube 20 against the distal end tip abutment 81a.

In this state, pinch and compress the compression unit 74 with fingers. In this time, the compression unit 74 is elastically deformed, and the insertion tube fixing part 85 holds the distal end coil 22 of the insertion tube 20. The insertion tube 20 is fixed in the axial direction (refer to FIG. 11).

Then, move the slider 42 shown in FIG. 1 and FIG. 2(B) to the distal end side, separating from the thumb ring 48. The wire 32 is moved to the distal end side of the insertion tube 20, through the first and second slide members 51 and 52 and wire receiving pipe 34. The arrowhead hook unit 31 connected to the distal end of the wire 32 is projected to the distal end tip 21 at the distal end of the distal end coil 22 of the insertion tube 20. Namely, the control wire 30 is moved, and the arrowhead hook unit 31 is projected to the distal end tip 21 at the end of the distal end coil 22 of the insertion tube 20.

Move the slider 42 farther to the distal end side, in the state that distal end of the arrowhead hook unit 31 contacts the conical hole formed in the elastic arm 62e of the connection member 62. The arms 61b of the clip 61 are elastically opened along the shape of the distal end of the clip housing 77, and the pipe 63 and connection member 62 are moved. The elastic arm 62e of the connection member 62 is expanded outward by the slope of the arrowhead hook unit 31. Push the arrowhead hook unit 31 further into the elastic arm 62e. When the arrowhead hook unit 31 passes through the elastic arm 62e, the elastic arm is elastically closed and the axis 31d is held by the elastic arm 62e. Therefore, the engaging part (large-diameter arrowhead part) 31a of the arrowhead hook unit 31 engages with the elastic arm 62a. The arrowhead hook unit 31 is held and locked by the elastic arm 62e, and the clip unit 60 is connected to the control wire 30.

Then, move the slider 42 toward the proximal end side. The clip unit 60 is pulled into the insertion tube 20 through the control wire 30, as shown in FIG. 12(A). At this time, the retractable wing 63d of the pipe 63 is pressed inward by the slope of the retractable wing diameter reducing part 81. Therefore, the retractable wing 63d is not caught by the end-face of the distal end tip 21, and the clip unit 60 is pulled into the insertion tube 20.

At this time, as shown in FIG. 12(B), the arms 61b of the clip 61 are closed to meet the inside diameter of the insertion tube 20. The retractable wing 63d of the pipe 63 is brought into contact with the inner surface of the insertion tube 20, and elastically deformed to keep the state housed in the pipe 63.

After the clip unit 60 is pulled into the insertion tube 20, weaken the force of the cartridge (clip case) 70 to pinch the compression unit 74. The compression unit 74 is expanded vertically by the elastic restoring force, and the insertion tube 20 can be removed from the insertion tube inserting part 80.

The clip unit 60 has been fitted to the distal end of the control wire 30 of the clip insertion apparatus 10. The distal end of the clip 61 of the clip unit 60 is in the state pulled in with respect to the distal end of the insertion tube 20.

Next, as shown in FIG. 13, insert the insertion tube 20 into the abdominal cavity through the surgical tool insertion channel 92 of the insertion section 90 of an endoscope previously inserted into the abdominal cavity, and lead the distal end of the insertion tube 20 to the part close to an object area while observing the abdominal cavity through an endoscope.

Next, an explanation will be given on the procedure of clipping a tissue of a patient by using the clip 61.

By pushing the slider 42 shown in FIG. 1 and FIG. 2(B) to the distal end side, the clip unit 60 is moved further in the insertion tube 20 through the control wire 30. As the distal end pipe 63a of the pipe 63 is formed in the sloped outside diameter part so that the outside diameter gradually becomes small advancing to the distal end to ensure smooth sliding in the insertion tube 20, the distal end pipe smoothly moves in the insertion tube 20 in this time. This is particularly effective when the insertion section 90 of an endoscope is bent with a small radius of curvature, as shown in FIG. 13.

Move the control wire 30 farther by operating the slider 42. The clip unit 60 projects from the insertion tube 20, as shown in FIG. 14(A). As the retractable wing 63d of the pipe 63 is on the downward slope toward the distal end side, the clip unit 60 is pushed out smoothly without resistance at this time. The retractable wing 63d of the pipe 63 is released from the state contacting the inner surface of the insertion tube 20, and projected to the periphery of the pipe 63. The pair of arms 61b of the clip 61 has an expanding characteristic, and opened to a certain extent immediately after being projected from the insertion tube 20.

Then, move the slider 42 to the proximal end side. The control wire 30 is moved back to the proximal end side, and the end-face of the proximal end side of the retractable wing 63d of the pipe 63 engages with the end-face of the distal end tip 21, as shown in FIG. 14(B).

Move the slider 42 farther to the proximal end side to move back the control wire 30 farther. The loop 61a of the clip 61 is pulled into the pipe 63 through the connection member 62, and the clip 61 is opened further, as shown in FIG. 14(C). The projection 61d of the clip 61 comes into contact with the inside step 63f of the pipe 63, and arms 61b are opened maximum.

Approach the clip 61 to an object area while observing the object area of a tissue of a patient through an endoscope, and apply the tissue grasping parts 61c of the clip 61 to the object area. At this time, insert the thumb into the thumb ring 48 of the control unit 40, and hold the slider 42 with forefinger and middle finger. The thumb ring 48 is rotatable with respect to the control unit main body 41.

Release the slider 42 as shown in FIG. 15(A). Hold the rotary grip 41b of the main body 41 of the control unit by the left hand, while holding the thumb ring 48 by the right hand, and rotate the main body 41 about the axis. The wire 32 is rotated through the first slide member (wire receiving pipe holder) 51 and wire receiving pipe 34. Namely, the hook unit 31 is rotated. Therefore, as shown in FIG. 15(B), a force is applied from the flat part 31c provided in the clip unit engaging part 31a of the hook unit 31 to the flat part 62j on the inner surface of the cutout 62d of the connection member 62 of the clip unit 60. The clip unit 60 is rotated about the axis as the hook unit 31 is rotated. When changing the direction by rotating the clip unit 60, rotate the main body 41 of the control unit by holding the rotary grip 41b of the main body. The main body 41 can also be rotated while keeping the thumb inserted into the thumb ring 48.

Move the slider 42 farther to the proximal end side. The control wire 30 is moved back, and the arms 61b of the clip 61 are pulled into the pipe 63 through the connection member 62. Therefore, the projection 61d of the clip 61 is engaged in the inside step 63f of the pipe 63, and the arms 61b of the clip 61 are closed as shown in FIG. 16(A). A tissue of a patient is securely grasped between the arms 61b of the clip 61. As the pipe 63 is made of resin with an appropriate elasticity more flexible than the clip 61, the projection 61d of the clip 61 is engaged in the inside wall of the pipe 63, and the clip 61 is prevented from moving in the axial direction inside the pipe 63, and kept closed.

Move the slider 42 farther to the proximal end side to move back the control wire 30. The thin-diameter part 62f (refer to FIG. 8(A)) as a breaking part of the connection member 62 of the clip 61 is broken as shown in FIG. 16(B). Therefore, the clip 61 and pipe 63 are released from the connection member 62. The clip 61 and pipe 63 of the clip unit 60 are separated from the clip insertion apparatus 10, and left in the abdominal cavity while grasping a tissue of a patient.

After leaving the clip 61, remove the clip insertion apparatus 10 from the surgical tool insertion channel 92 of the insertion section 90 of the endoscope. To reload the clip unit 60, remove the connection member 62 from the arrowhead hook unit 31. In this case, by opening the elastic arm 62e of the connection member 62, the arrowhead hook unit 31 can be removed from the cutout 62d of the connection member 62.

Next, an explanation will be given on the effects of the structure connecting the proximal end coil 24 of the insertion tube 20 and control unit 40.

The proximal end of the proximal end coil 24 of the insertion tube 20 of this embodiment is merely inserted into the guide pipe 43, and not fixed by welding or bonding. The proximal end coil 24 is held between the proximal end-face of the coil insertion hole 41d of the guide pipe and the supporter mount 46 with a clearance (play) in the axial direction. The control unit 40 and insertion tube 20 are freely rotatable with each other.

Therefore, the insertion tube 20 is prevented from twisting when the rotary grip 41b of the control unit 40 is rotated about the axis of the main body 41 in order to rotate the clip unit 60. Unnecessary repulsion is not generated between the control unit 40 and insertion tube 20, and the rotating force is efficiently transmitted only to the control wire 30 by the rotation of the rotary grip 41b of the main body 41. Therefore, by turning the rotary grip 41b of the main unit 41 about the axis of the main body 41, the clip unit 60 can be smoothly rotated through the control wire 30.

These effects are applied not only to the clip insertion apparatus 10, but also all surgical tools operated by rotating a surgical part by the control wire 30.

Next, an explanation will be given on the effects of the structure that the wire receiving pipe 34 is fixed to the proximal end of the wire 32.

The wire receiving pipe 34 is shaped flat as shown in FIG. 4(B) by swaging. The fixing part 51j of the first slide member 51 is shaped corresponding to the flat form of the wire receiving pipe 34, and presses the flat part of the wire receiving pipe 34 in the vertical direction, for example. Therefore, when the first slide member 51 is rotated, the wire receiving pipe 34 is also rotated. The rotating force of the rotary grip 41b of the main body 41 can be securely transmitted to the wire 32 through the fixing part 51j of the first slide member 51 of the slider 42, wire receiving pipe 34 and control pipe 33.

These effects are applicable not only to the clip insertion apparatus 10, but also all surgical tools operated by rotating a surgical part by the control wire 30.

Next, en explanation will be given on the effects of the O-ring 44 provided in the periphery of the control pipe 33.

As shown in FIG. 3, the O-ring 44 is provided on the periphery of the control pipe 33, and fastens the control pipe 33 in the radial direction. The O-ring 44 is softly fit not to be moved by a force like a self-weight of the slider 42 or main body 41. Therefore, even if the operator releases a finger from the slider 42 during loading or rotating the apparatus, the control pipe 33 is held engaged with the main body 41 by the frictional force between the O-ring 44 and control pipe 33, and the slider 42 is not inadvertently moved. This prevents accidental pop-up of the clip unit 60 or hook unit 31, when the tension of the wire 32 is relived (released).

Particularly, when a finger is put on the slider 42 during rotating the rotary grip 41b, a tensile force is generated in the control wire 30, and the retractable wing 63d of the pipe 63 of the clip unit 60 and the end-face of the distal end tip 21 of the insertion tube 20 are pressed. Namely, a strong frictional force is generated between the non-rotating insertion tube 20 and the rotating retractable wing 63d. Thus, the control wire 30 provided at the distal end of the clip unit 60 is not easily rotated. That is, the clip unit 60 is not smoothly rotated. Therefore, though the slider 42 should be released during rotating the rotary grip 41b, the slider 42 is softly fit by the O-ring 44 not to move easily, and the rotary grip 41b can be reliably operated.

As shown in FIG. 3, the tensile force of the control wire 30 is securely relieved during turning the rotary grip 41b, and the O-ring housing 43a of the guide pipe 43 has a clearance (play) to permit the O-ring to move 2-6 mm back and forth. If the slider 42 is released in this time, the tensile force of the wire 32 is securely relieved (released). Namely, the whole control wire 30 is moved to the distal end side. Therefore, if the slider 42 is released in the state that the proximal end of the retractable wing 63d contacts the end of the distal end tip 21, the contact between the end of the distal end tip 21 and the proximal end of the retractable wing 63d is relieved. Namely, the frictional force acting between the end of the distal end tip 21 and the proximal end of the retractable wing 63d is decreased or completely eliminated. Then, as shown in FIG. 15(A), when the control unit main body 41 is rotated, no frictional force is generated between the end of the distal end tip 21 and the proximal end of the retractable wing 63d, and the clip unit 60 can be easily rotated.

These effects are applicable not only to the clip insertion apparatus 10, but also all surgical tools operated by rotating a surgical part.

Next, an explanation will be given on the effects of the structure of the first slide member 51 of the slider 42.

As shown in FIG. 2(B), the length between the slit applying surfaces 51m and 51n of the first slide member 51 is set shorter than the length of the whole slider 42. Therefore, the distal end side of the slide member 52 of the slider 42 is movable to the distal end side passing over the slit 41a. The total length of the main body 41 can be reduced while ensuring the moving range of the slider 42. This increases the ease of handling, when sealing the clip insertion apparatus in a sterilized pack, for example.

These effects are applicable not only to the clip insertion apparatus 10, but also all surgical tools.

Next, an explanation will be given on the effects of the coil connecting pipe 23 in the state that an angle portion of the insertion section 90 of the endoscope is bent.

Figure 17:
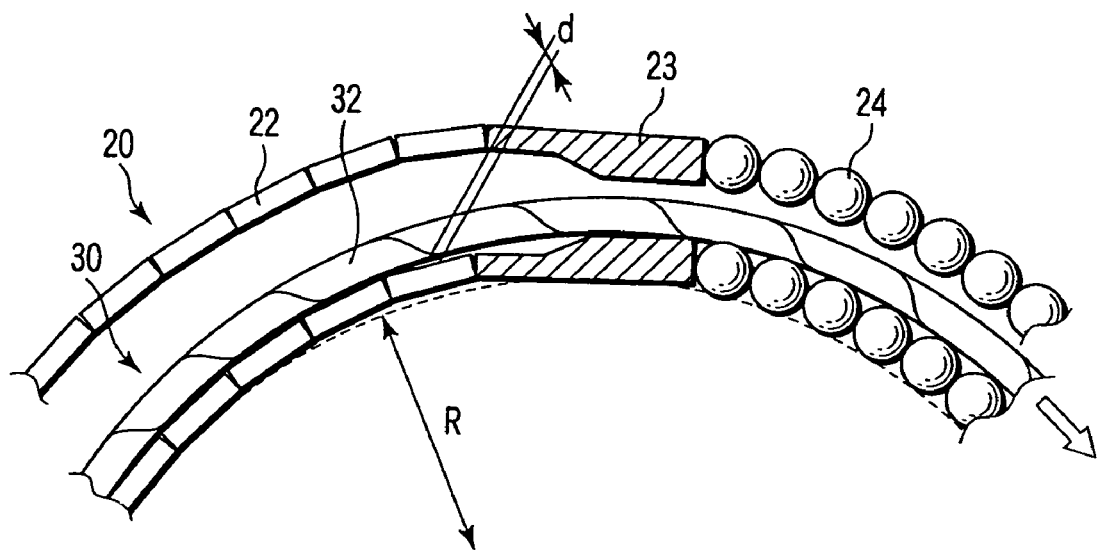
FIG. 17 is a schematic sectional view showing the state that the insertion tube of the clip insertion apparatus according to the first embodiment is bent, and a wire is set along the inner surfaces of the distal end coil, coil connection pipe and proximal end coil.

FIG. 17 shows the states of the proximal end of the distal end coil 22, the coil connecting pipe 23 and the distal end of the proximal end coil 24 of the clip insertion apparatus 10 inserted into the surgical tool insertion channel 92 of the insertion section 90, when the insertion section 90 (refer to FIG. 13) of the endoscope is bent with a relatively small radius (R). The insertion tube 20 of the clip insertion apparatus 10 connects the distal end coil 22 and proximal end coil 24 through the coil connecting pipe 23 interposed therebetween.

Figure 18:
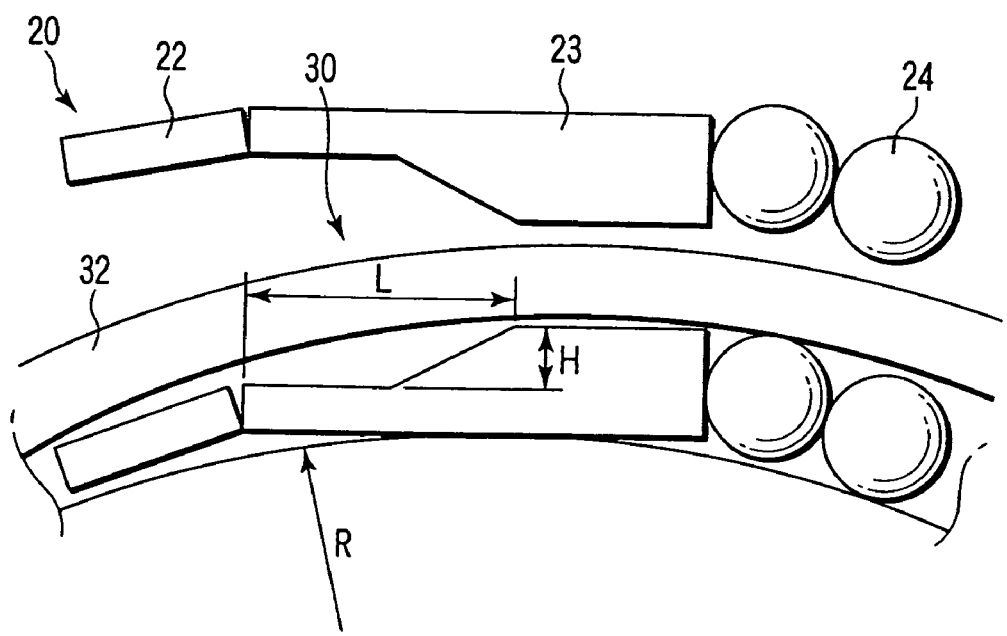
FIG. 18 is a schematic sectional view showing a value H obtained by subtracting the thickness of the distal end coil from the thickness of the proximal end coil, and a length L of the distal end side of a coil connection pipe determined by the radius R of the insertion portion bent maximum, in the state that the insertion tube of the clip insertion apparatus according to the first embodiment is bent, and a wire is set along the inner surfaces of the distal end coil, coil connection pipe and proximal end coil.

As shown in FIG. 18, the inner surface of the coil connecting pipe 23 is gradually changed to decrease the diameter from the inside diameter of the distal end coil 22 to the inside diameter of the proximal end coil 24, to meet the travel by the pulling force of the control wire 30 when the insertion section 90 of the endoscope is bent. Therefore, a gap d formed between the distal end coil 22 and control wire 30 shown in FIG. 17 is decreased by the inside shape of the coil connecting pipe 23 to meet the travel of the control wire 30, when the insertion section 90 of the endoscope is bent to the bending radium R.

The reference numeral H in FIG. 18 indicates the value obtained by subtracting the thickness of the distal end coil 22 from the thickness of the proximal end coil 24, for example. The reference numeral L indicates the length of the distal end side of the coil connecting pipe 23 determined by the reference numeral H and the bending radius R, when the insertion section 90 is bent maximum.

Since the length and diameter of the coil connecting pipe 23 are adjusted so that the inside diameter of the proximal end of the distal end coil 22 is smoothly connected to the inside diameter of the distal end of the proximal end coil 24, the gap d between the proximal end of the distal end coil 22 and control wire 30 can be reduced. Therefore, the distal end coil 22 is not deformed and the strand is not displaced, even if a strong pulling force is applied to the control wire 30 in the state that the insertion section 90 is bent maximum.

Figure 19:
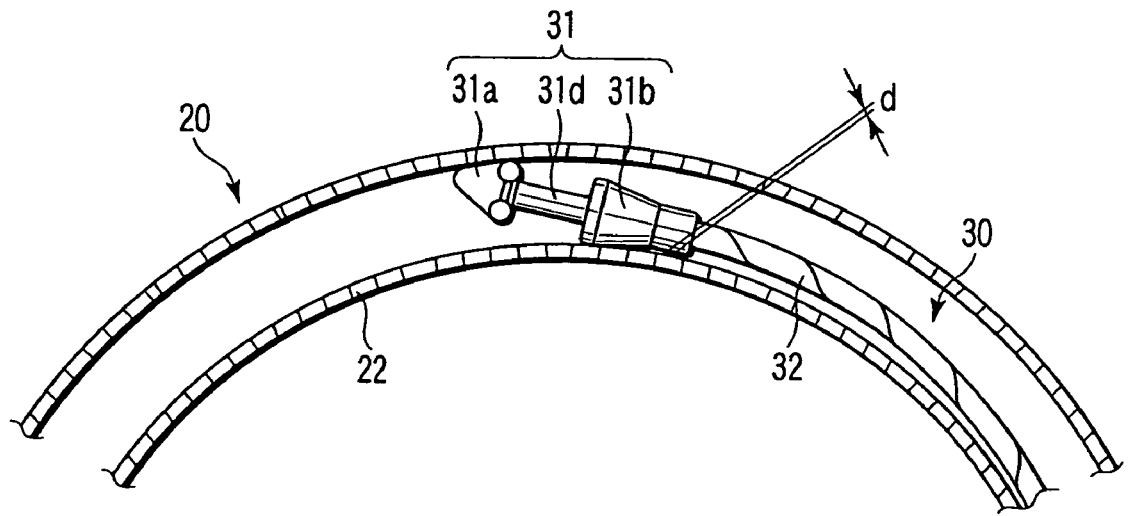
FIG. 19 is a schematic sectional view showing the state that the insertion tube of the clip insertion apparatus according to the first embodiment is bent, and the control wire is set along the insertion tube.

As shown in FIG. 19, in the engaging part 31a of the hook unit 31 of the control wire 30 and the wire connecting part 31b of the hook unit 31 that is a part of connecting to the wire 32, the outside shape of the wire 32 side is reduced in diameter and substantially conical compared with the engaging part 31a of the hook unit 31. Namely, the outside shape of the connecting part 31b is tapered. Therefore, a part of the outer surface of the wire connecting part 31b makes surface contact with the inner surface of the distal end coil 22, when the control wire 30 is moved by the pulling force.

As the wire connecting part 31b of the hook unit 31 is shaped substantially conical, the gap d between the wire connecting part 31b/wire 32 and the inner surface of the distal end coil 22 can be reduced. Therefore, the distal end coil 22 is not deformed and the strand is not displaced, even if a strong pulling force is applied to the control wire 30 in the state that the insertion section 90 is bent maximum.

The effects explained with reference to FIG. 17 to FIG. 19 is applicable not only to the clip insertion apparatus 10, but also all surgical tools using the coil 22 in the insertion tube (outer tube) 20.

As explained hereinbefore, the following effects can be obtained in this embodiment.

By making the inside diameter of the coil connecting pipe 23 large in the distal end side and small in the proximal end side, just like tapered, the gap d between the proximal end of the distal end coil 22 and control wire can be reduced, when the insertion tube 20 is bent. Therefore, the distal end coil 22 is not deformed and the strand is not displaced, even if a strong pulling force is applied to the control wire 30 in the state that the insertion section 90 is bent maximum. The distal end coil 22 is prevented from buckling, even if the insertion apparatus 10 is inserted into the channel 92 and a strong pulling force is applied to the control wire 30 in the state the insertion section 90 of an endoscope is bent maximum.

In the clip insertion apparatus 10 in which the control wire 30 is operated by a strong force, even if the insertion tube 20 made by connecting two coils 22 and 24 with different inside diameters is used, the strand of the distal end coil 22 is not displaced in the area close to the part connecting the coils. This makes it possible to provide an insertion apparatus having excellent durability and smoothness of insertion into the insertion section of the endoscope.

The wire connecting part 31b of the hook unit 31 is shaped substantially conical to have a diameter larger in the distal end side and little larger than the outside diameter of the wire 32 in the proximal end side (reduced in the diameter). Therefore, when the insertion tube 20 is bent, the gap d between the proximal end of the wire connecting part 31b and the inner surface of the distal end coil 22 can be reduced. Even if a strong pulling force is applied to the control wire 30 in the state that the insertion section 90 is bent maximum, the wire connecting part 31b of the hook unit 31 prevents deformation of the distal end coil 22 and displacement in the strand of the distal end coil 22. The buckling of the distal end coil 22 is prevented, even if a strong pulling force is applied to the operation coil 30 in the state that insertion section 90 of an endoscope is bent maximum and the insertion apparatus 10 is inserted into the channel 92 of the insertion section 90.

In the clip insertion apparatus 10 in which the control wire 30 is operated by a strong force, as the outside shape of the wire connecting part 31b is tapered to decrease the diameter toward the proximal end side, the strand of the distal end coil 22 is not displaced in the area close to the part connecting the wire connecting part 31b and wire 32. This makes it possible to provide an insertion apparatus having excellent durability and smoothness of insertion into the insertion section of the endoscope.

The wire receiving pipe 34 is formed flat by swaging. The fixing part 51j of the wire receiving pipe holder (first slide member) 51 is formed to meet the flat shape of the wire receiving pipe 34, to be held vertically by the flat part. Therefore, when the wire receiving pipe holder 51 is rotated, the wire receiving pipe 34 is also rotated and the rotating force is securely transmitted to the control wire 30.

The O-ring 44 fastens the control pipe 33, and is softly fit not to be moved by a force like a self-weight of the slider 42 or main body 41. Therefore, even if the operator releases a finger from the slider 42 during loading or rotating the apparatus, the slider 42 is not inadvertently moved. This prevents accidental pop-up of the clip unit 60 or hook unit 31 from the insertion tube 20.

Particularly, when a finger is put on the slider 42 during the rotating operation, a tensile force is generated in the control wire 30, the retractable wing 63d and the end-face of the distal end tip 21 of the insertion tube 20 are pressed with each other, and a strong frictional force is generated. Thus, the clip unit 60 is not smoothly rotated, and it is necessary to release a finger from the slider 42 during the rotating operation. The O-ring 44 fastening the slider 42 ensures stable rotating operation.

The O-ring housing 43a of the guide pipe 43 has a clearance to permit the O-ring 44 to move 2-6 mm back and forth. The tensile force is securely released by releasing the slider 42. Therefore, the clip unit 60 can be easily rotated.

The length between the slit applying surfaces 51*m* and 51*n* of the wire receiving pipe holder (first slide member) 51 is set shorter than the length of the whole slider 42. Therefore, the distal end side of the slider 42 is movable to the distal end side passing over the slit 41*a*. This reduces the whole length of the main body 41 while ensuring the moving range of the slider 42, and increases the ease of handling when sealing the clip insertion apparatus in a sterilized pack.

Next, a second embodiment will be explained with reference to FIG. 20. This embodiment is modified from the first embodiment. The same reference numerals are given to the same components, and a detailed explanation will be omitted.

Figure 20:
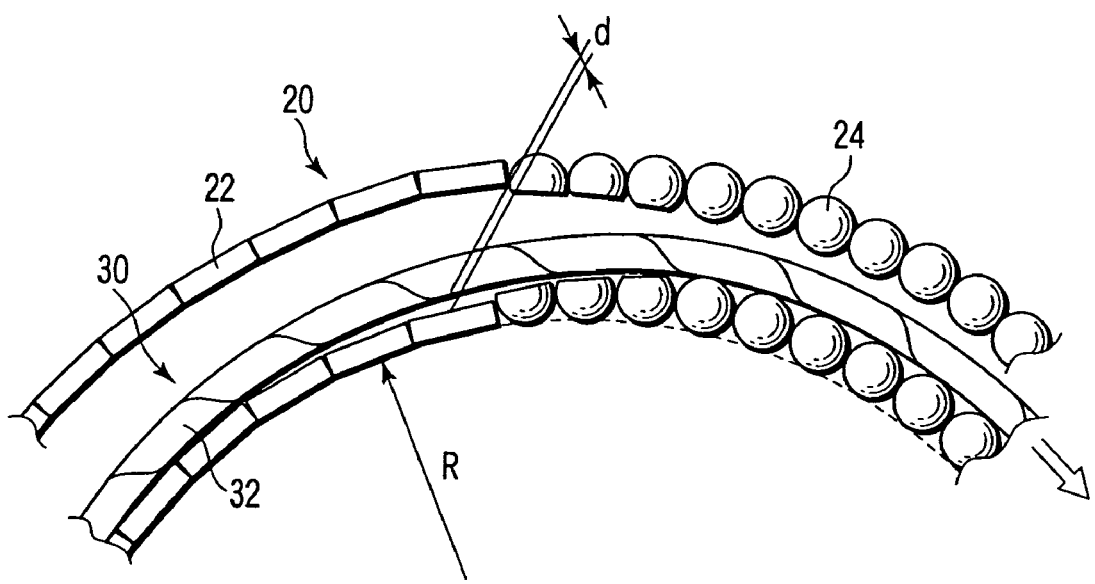
FIG. 20 is a schematic sectional view showing an insertion tube of a clip insertion apparatus according to a second embodiment, and the state that the insertion tube is bent, and a wire is set along the inner surfaces of the distal end coil and proximal end coil.

As shown in FIG. 20, the insertion tube 20 of the clip insertion apparatus 10 of this embodiment includes a distal end tip 21, a distal end coil 22, a proximal end coil 24, and a coil receiving pipe 25. Namely, the coil connecting pipe 23 (refer to FIG. 17 and FIG. 18) is eliminated.

The inside diameter of the proximal end of the proximal end coil 24 is made smaller than the inside diameter of the distal end coil 22, although not shown in the drawing. The proximal end coil 24 is tapered in the distal end part to increase the inside diameter gradually from the distal end side to the proximal end side. The inside diameter of the distal end of the proximal end coil 24 is formed to be substantially the same as the inside diameter of the proximal end of the distal end coil 22.

The inner surface of the proximal end coil 24 is gradually changed to decrease the diameter from the large inside diameter of the distal end side to the small inside diameter of the proximal end, to meet the travel by the pulling force of the control wire 30, when the insertion section 90 of the endoscope is bent. Therefore, a gap d formed between the distal end coil 22 and control wire 30 is decreased by the inside shape of the distal end of the proximal end coil 24, meeting the travel of the control wire 30, when the insertion section 90 of the endoscope is bent to the bending radium R.

As the inside diameter of the distal end of the proximal end coil 24 is adjusted so that the inside diameter of the proximal end of the distal end coil 22 is smoothly connected to the inside diameter of the distal end of the proximal end coil 24, the gap d between the proximal end of the distal end coil 22 and control wire 30 can be reduced. Therefore, the distal end coil 22 is not deformed and the strand is not displaced, even if a strong pulling force is applied to the control wire 30 in the state that the insertion section 90 is bent maximum.

As explained hereinbefore, the following effects can be obtained in this embodiment.

By making the inside diameter of the coil 24 neat at hand large in the distal end side and small in the proximal end side, just like tapered, the gap d between the proximal end of the distal end coil 22 and control wire can be reduced. Therefore, the distal end coil 22 is not deformed and the strand is not displaced, even if a strong pulling force is applied to the control wire 30 in the state that the insertion section 90 is bent maximum.

Figure 21:
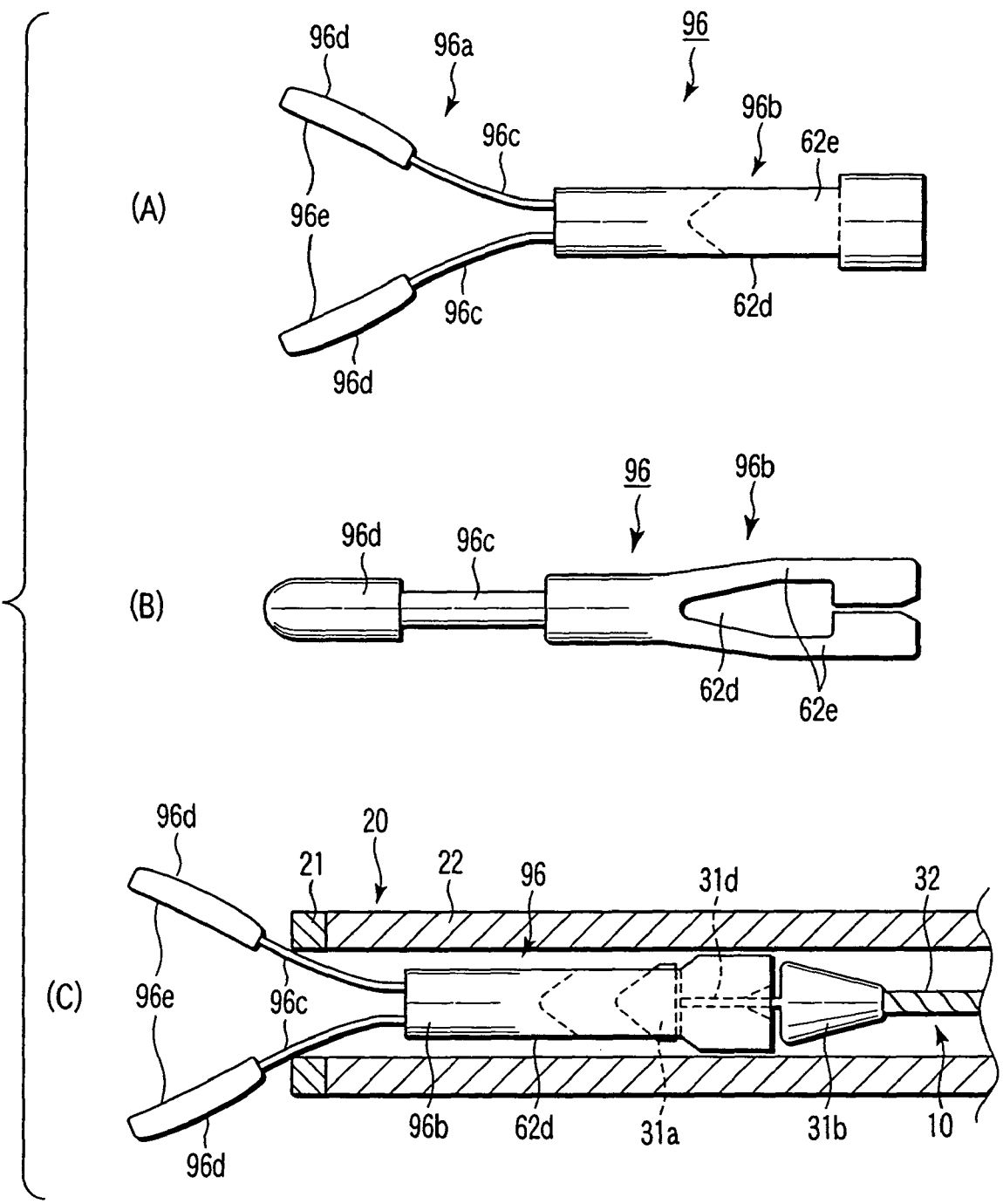
FIGS. 21(A) and (B) are schematic plane views showing a grasping forceps according to a third embodiment.
FIG. 21(C) is a partially sectional schematic view showing the state that the grasping forceps are connected to the insertion apparatus.

Next, a third embodiment will be explained with reference to FIGS. 21(A) to 21(C).

A surgical tool operated by the clip insertion apparatus explained in the first embodiment is not limited to the clip unit 60. For example, a grasping forceps 96 shown in FIGS. 21(A) and 22(B) can be used. The grasping forceps 96 includes a tissue grasping part 96*a*, and a connection member 96*b*. The proximal end of the connection member 96*b* has the same structure as the connection member 62 explained in the first embodiment, and an explanation will be omitted. In the following description, the same components as those of the connection member 62 are given the same reference numerals, and an explanation will be omitted. The distal end of the connection member 96*b* is connected to the proximal end of the tissue grasping part 96*a* as a one-piece structure. The grasping part 96*a* includes a pair of arms 96*c*, and a pair of grasping hands 96*d*. The proximal end of the arm 96*c* is fixed to the distal end of the connection member 96*b*. The grasping hand 96*d* is fixed to the distal end of the arm 96*c*. The grasping hand 96*d* has a grasping surface 96*e* formed wide for grasping a tissue. It is also preferable to form the grasping surface 96*e* rough to produce friction with a tissue 100.

The pair of arms 96*c* is made of elastic material. The arms 96*c* are narrow in the proximal end side, or the distal end of the connection member 96*b*, and gradually become wide toward the distal end side. Therefore, the arms 96*c* are increased and decreased in the width of the distal end by elastic deformation.

An explanation will now be given on the effects in a surgical treatment by connecting the grasping forceps to the insertion apparatus (clip insertion apparatus) 10, just like the clip unit 60.

Just like providing the clip unit 60 in the cartridge 70 (refer to FIG. 10(A) for example) in the first embodiment, provide the grasping forceps 96 in the cartridge 70. At this time, the connection member 96*b* of the grasping forceps 96 has been provided in the connection member housing 79 of the cartridge 70.

Insert the distal end tip 21 of the insertion tube 20 all the way to the butt-up 81*a* through the insertion tube inserting part 80 of the cartridge 70. In this state, project the engaging part 31*a* from the distal end of the insertion tube 20, and push the proximal end of the connection member 96*b* toward the distal end side of the cartridge 70. The pair of arms 96*c* of the grasping part 96*a* are gradually opened, and the connection member 96*b* is moved to the distal end side. Therefore, the connection member 96*b* of the grasping forceps 96 is placed in the expanded part 79*a* of the elastic arm, and the proximal end of the connection member 96*b* is engaged with the engaging part 31*a* of the control wire 30.

In this state, pull the wire 32 of the control wire 30 into the proximal end side, and place the grasping forceps 96 in the insertion tube 20. Place the insertion tube 20 with the proximal end of the grasping forceps 96 engaged with the engaging part 31*a* in the abdominal cavity, by inserting through the surgical tool insertion channel of the endoscope. Namely, project the distal end of the insertion tube 20 from the end of the surgical tool insertion channel 92.

Move the wire 32 of the control wire 30 to the distal end side, and project the grasping forceps 96 from the end of the insertion tube 20. Rotate the grasping forceps 96, align the direction, and grasp a tissue of a patient by the grasping surfaces 96*a* of the grasping hands 96*d* of the grasping forceps 96. At this time, project the insertion tube 20 farther from the end of the surgical tool insertion channel 92. Then, the connection member 96*b* of the grasping forceps 96 is relatively pulled into the inside hole of the insertion tube 20, and the pair of arms 96*c* contact the inner peripheral edge of the distal end of the insertion tube 20. When the grasping forceps 96 are pulled further into the inside hole of the insertion tube 20, the arms 96*c* contacting the inner peripheral edge of the distal end of the insertion tube 20 is elastically deformed and pulled to the inside of the insertion tube 20 by gradually approaching the both from the proximal end side to the distal end side. Namely, the end of the insertion tube 20 guides the pair of arms 96*c* in the closing direction. Therefore, the grasping hands 96*d* of the grasping forceps 96 are finally pulled into the inside hole of the insertion tube 20.

In this embodiment, the grasping surfaces 96e are formed in the grasping hands 96d. It is also preferable to make the grasping hands 96d cup-shaped. When the cup-shaped grasping hands 96d are put in the inside hole of the insertion tube 20, the grasping hands 96d are preferably put together in substantially an egg-like closed state.

Figure 22:
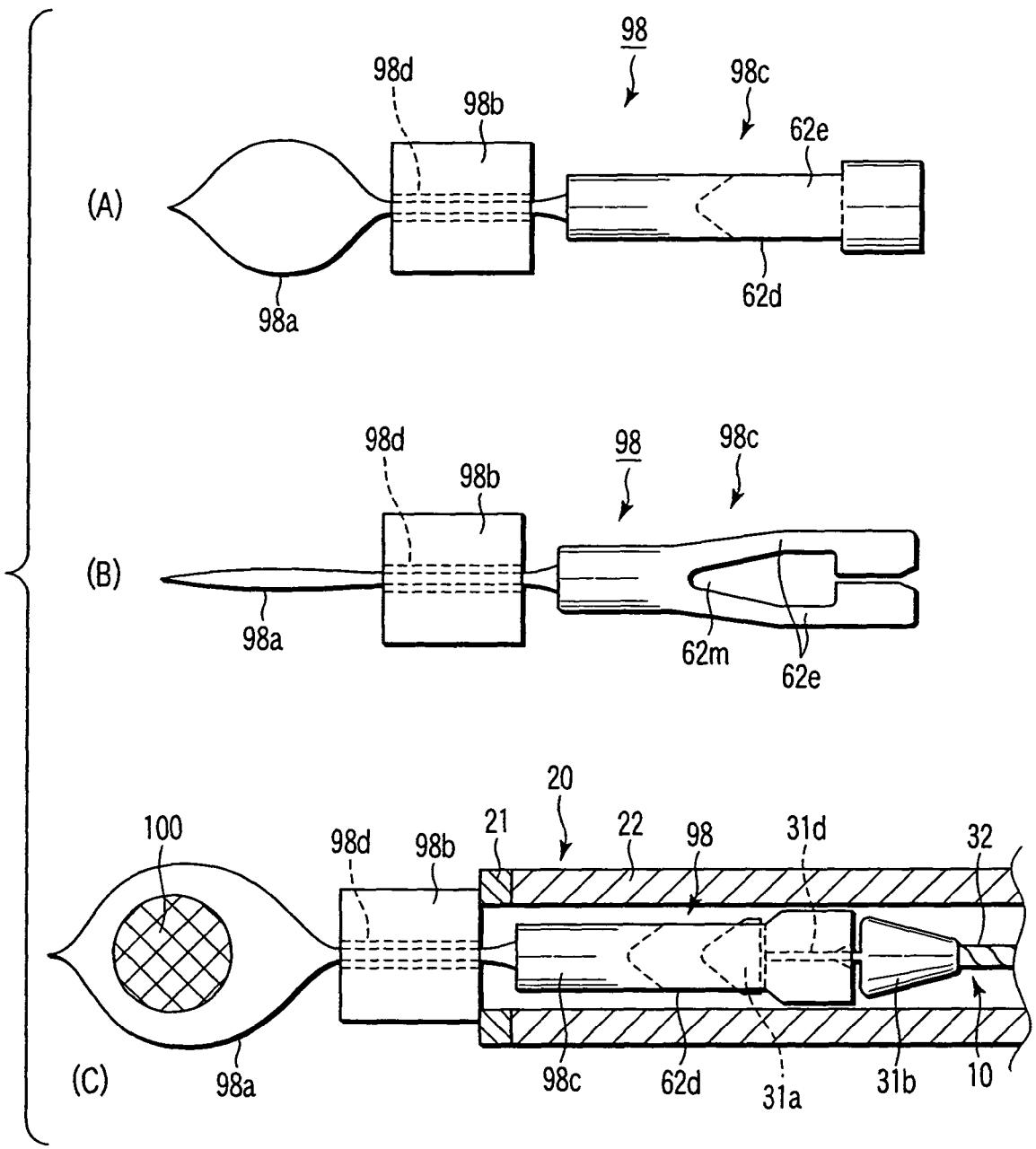
FIGS. 22(A) and (B) are schematic plane views showing a stay snare according to a fourth embodiment.
FIG. 22(C) is a partially sectional schematic view showing the state that the stay snare is connected to the insertion apparatus.
Figure 23:
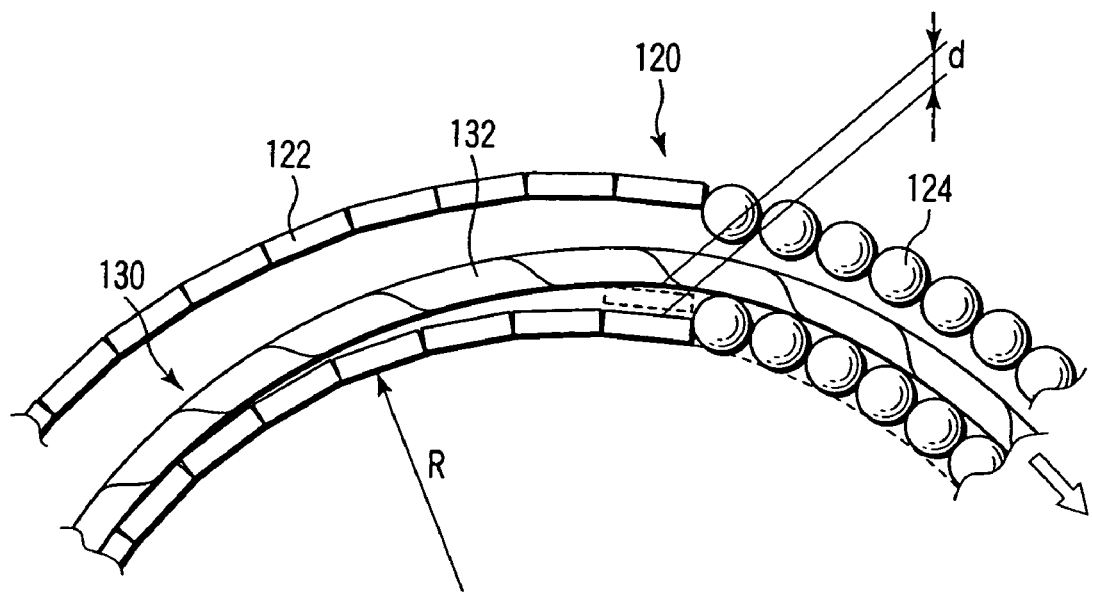
FIG. 23 is a schematic sectional view showing the state that an insertion tube of a clip insertion apparatus according to a prior art is bent, and a wire is set along on the inner surfaces of the distal end coil and proximal end coil.
Figure 24:
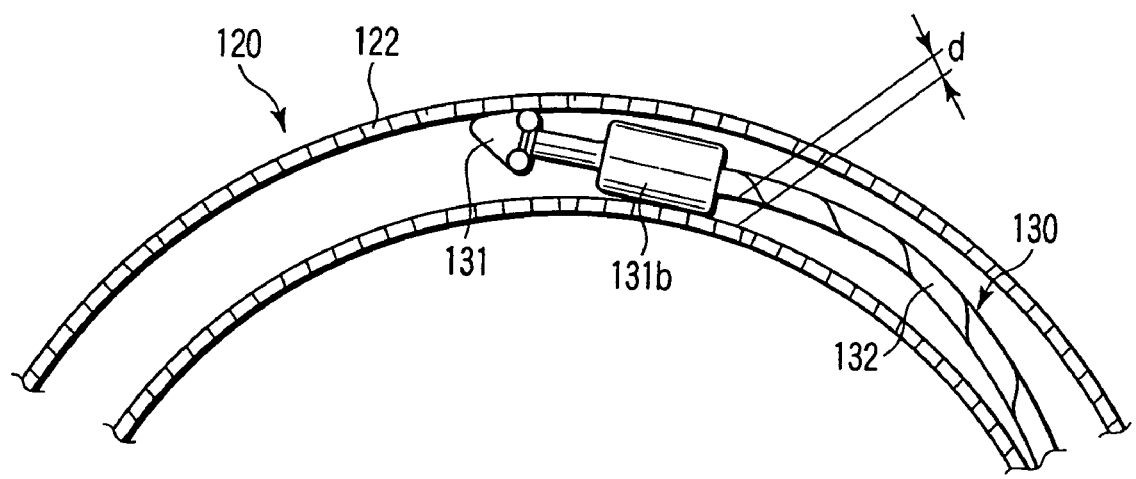
FIG. 24 is a schematic sectional view showing the state that an insertion tube of a clip insertion apparatus according to a prior art is bent, and a control wire is set along the insertion tube.

Next, a fourth embodiment will be explained by referring to FIGS. 22(A) to 22(C). This embodiment is modified from the first embodiment.

The surgical tool operated by the clip insertion apparatus 10 explained in the first embodiment is not limited to the clip unit 60 and grasping forceps 96. For example, a stay snare 98 shown in FIGS. 22(A) and 22(B) can be used. The stay snare 98 includes a snare 98a, a stopper 98b and a connection member 98c. The loop-shaped snare 98a is fixed to the distal end of the connection member 98c. The stopper 98b is provided slidable to the snare 98a in the distal end side of the connection member 98c, or the proximal end of the snare 98a. The stopper 98b is formed substantially cylindrical, and provided with a through hole 98d in the central axis. The snare 98a is inserted into the through hole 98d. The outside diameter of the stopper 98b is larger than the inside diameter and smaller than the outside diameter of the distal end tip 21 of the insertion tube 20. The stopper 98b is made of material such as PTFE with high sliding smoothness for the inside wall of the snare 98a and surgical tool insertion channel 92, and the peripheral edge of its end is preferably chamfered. Therefore, the stopper 98b can be abutted against the end of the distal end tip 21, and can be inserted into the surgical tool insertion channel 92 of the endoscope together with the insertion tube 20.

An explanation will now be given on the effects in a surgical operation by connecting the snare 98 to the insertion apparatus (clip insertion apparatus), just like the clip unit 60 and grasping forceps 96.

As in the first and second embodiments, the stay snare 98 is previously placed in a cartridge having an appropriate shape. The cartridge has at least a part having a diameter capable of ejecting the stopper 98b. The stay snare 98 is not necessarily placed in a cartridge.

Engage the engaging part 31a at the distal end of the control wire 30 with the proximal end of the connection member 98c of the stay snare 98. Pull the connection member 98c into the inside hole of the insertion tube 20, in the state that the proximal end of the stopper 98b contacts the distal end of the insertion tube 20. Pull the wire 32 of the control wire 30 into the proximal end side to by the distance that the snare 98a is not removed from the stopper 98b, and place the connection member 98c of the stay snare 98 in the insertion tube 20. Insert the insertion tube 20 with the proximal end of the stay snare 98 engaged with the engaging part 31a, into the surgical tool insertion channel 92 of the endoscope, and place the snare in an abdominal cavity. As the stopper 98b is smaller than the outside diameter of the insertion tube 20 and has high sliding smoothness for the inside wall of the surgical tool insertion channel 92, the distal end of the insertion tube 20 can be projected from the end of the surgical tool insertion channel 92.

Move the wire 32 of the control wire 30 to the distal end side, and project the snare 98a and stopper 98b of the stay snare 98 from the distal end of the insertion tube 20. Place the snare 98a of the stay snare 98 around a tissue 100 of a patient. Namely, hang the snare 98a on the projected tissue 100. Pull the wire 32 to the proximal end side, and project the insertion tube 20 farther from the surgical tool insertion channel 92. Then, the loop diameter of the snare 98a fixed to the connection member 98c is reduced, in the state that the stopper 98b contacts the distal end chip 21. Therefore, the tissue 100 is bound.

Remove the stay snare 98 from the insertion apparatus 10, in the state that the snare 98a is binding the tissue 100. Concretely, pull the insertion tube 20 into the control wire 30 without moving the control wire 30. The connection member 98c of the stay snare 98 projects from the end of the insertion tube 20. Pull the whole insertion apparatus to the proximal end side in this state. The elastic arms 62e are unable to withstand the tensile force, and opened by the elastic force. Therefore, the stay snare 98 is disengaged from the control wire 30, and the snare 98 is left in the state binding the tissue 100.

The surgical tool is not limited to the clip unit 60, grasping forceps 96 and stay snare 98. Other various tools may be used.

Although the invention has been concretely explained in terms of preferred embodiments with reference to the accompanying drawings, it will be noted that the invention is not limited to the embodiments. The invention may include all forms embodied without departing from its spirit or essential characteristics.

According to the above description, the following items of the invention are obtained. Each item may be combined.

[Additional Notes]

1. An insertion apparatus (10) for a flexible endoscope comprising:

an insertion tube (20) having a distal end coil (22), and a proximal end coil (24) which is provided concentrically with the proximal end of the distal end coil, and has an inside diameter smaller than that of the distal end coil; and a control wire (30) which is movably inserted in the insertion tube, wherein the proximal end coil has an inside shape, in which a gap (d) between the inner surface of the distal end coil and the outside of the control wire in an area close to a connection part between the distal end coil and proximal end coil becomes smaller than the amount of deformation exceeding an allowable stress of the distal end coil, when the control wire is placed along the inner surfaces of the distal end coil and proximal end coil in the central side of bending, in the state the insertion tube is bent to a shape with a radius of 10 to 30 mm.

2. An insertion apparatus (10) for a flexible endoscope comprising:

an insertion tube (20) having a distal end coil (22), a proximal end coil (24) which is provided in the proximal end side of the distal end coil and has an inside diameter smaller than that of the distal end coil, and a connection member (23) which is provided between the distal end coil and proximal end coil and connects the distal end coil and proximal end coil; and a control wire (30) which is movably inserted into the insertion tube, wherein at least one of the connection member and proximal end coil has an inside shape, in which a gap between the inner surface of the distal end coil and the outer surface of the control wire in an area close to the connection member becomes smaller than the amount of deformation exceeding an allowable stress of the distal end coil, when the control wire is placed along the inner surfaces of the coils in the central side of bending, in the state the insertion tube including the connection member is bent to a shape with a radius of 10 to 30 mm.

3. The insertion apparatus (10) according to item 2, wherein the connection member (23) has an inside shape to increase an inside diameter gradually toward the distal end side.

4. The insertion apparatus (10) according to item 1 or 2, wherein the proximal end coil (24) has an inside shape tapered to increase a diameter gradually toward the distal end side.

5. An insertion apparatus (10) for a flexible endoscope comprising:
coils (22, 24);
a control wire (30) which is movably inserted into the coil;
a hard member (31) which is provided on the control wire, and has an outside diameter larger than the outside diameter of the control wire,
wherein the hard member has an inside shape, in which a gap between the inner surfaces of the coils and the proximal end of the hard member becomes smaller than the amount of deformation exceeding an allowable stress of the coils, when the control wire is placed along the inner surfaces of the coils in the central side of bending, in the state the coils are bent to a shape with a radius of 10 to 30 mm.

6. The insertion apparatus (10) according to item 5, wherein the hard member (31) has an outside shape tapered to decrease a diameter from a maximum outside diameter part toward the proximal end side.

7. The insertion apparatus (10) according to any one of items 1 to 5, wherein a surgical tool (60) for a flexible endoscope is a clip insertion apparatus.

8. An insertion apparatus (10) for a flexible endoscope comprising:
an insertion tube (20) having a distal end coil (22), and a proximal end coil (24) which is provided concentrically with the proximal end of the distal end coil, and has an inside diameter smaller than that of the distal end coil; and
a control wire (30) which is movably inserted into the insertion tube,
wherein the proximal end coil has an inside diameter gradually increased toward the distal end side.

9. An insertion apparatus (10) for a flexible endoscope comprising:
an insertion tube (20) having a distal end coil (22), a proximal end coil (24) which is provided concentrically with the proximal end of the distal end coil and has an inside diameter smaller than the distal end coil, and a connection member (23) which connects the distal end coil and proximal end coil;
a control wire (30) which is movably inserted into the insertion tube,
wherein the connection member has an inside diameter gradually increased toward the distal end side.

10. An insertion apparatus (10) for a flexible endoscope comprising:
an insertion tube (20);
a control wire (30) which is movably inserted into the insertion tube;
a hard member (31) which is provided on the control wire, and has an outside diameter larger than the outside diameter of the control wire,
wherein the hard member has an outside shape tapered to decrease a diameter from a maximum outside diameter part toward the proximal end side.

11. A surgical system for an endoscope comprising an insertion apparatus (10) for the endoscope inserted into an insertion section (90) of the endoscope, and a surgical tool (60) connected to the distal end of the insertion apparatus, wherein the insertion apparatus comprises:
a sheath (20);
a control wire (30) which is inserted into the sheath, and movable in the axial direction and about the axis; and
an engaging part (31) which is provided at the distal end of the control wire and configured to engage with the surgical tool; and
a control unit (40) which is provided at the proximal end of the sheath, and controls movement along the axial direction and rotation about the axis of the control wire,
the control unit comprises:
a control unit main body (41) which is provided at the proximal end of the sheath;
a slider (42) which is connected to the control wire, and slidable along the axial direction of the control wire with respect to the control unit main body; and
a movement control member (44) which is provided between the control unit main body and slider, and controls movement of the slider with respect to the control unit main body,
the operation unit main body is provided with the movement control member, and a movement allowing part (43a) which allows the movement control member to move along the axial direction of the control wire to release a tensile force of the control wire, and
the surgical tool is provided with a connection part (62) at the proximal end, which is connected to the engaging part of the insertion apparatus, brought into contact with the distal end of the sheath in the state that a tensile force is applied to the control wire, and released from the distal end of the sheath by the movement of the movement control member in the movement allowing part, when the tensile force of the control wire is released.

When a tensile force is applied to the control wire, the surgical tool is brought into contact with the distal end of the sheath by the tensile force. Therefore, the surgical tool is difficult to rotate even if the control wire is rotated. However, when the tensile force of the control wire is released by the movement allowing part, frictional force between the surgical tool and the distal end of the sheath is relieved, and when the control wire is rotated, the surgical tool is also easily rotated.

12. The surgical system for an endoscope according to item 11, wherein the movement control member (44) is provided with an O-ring (44), which contacts the control wire (30) on the inner surface, and separates from the movement allowing part (43a) on the outer surface.

Therefore, the surgical tool is prevented from rotating when a tensile force is applied to the control wire at low cost, and easily rotated with the rotation of the control wire when the tensile force is released.

13. A surgical system for an endoscope comprising an insertion apparatus (10) for the endoscope inserted into an insertion section (90) of the endoscope, and a surgical tool (60) connected to the distal end of the insertion apparatus,
wherein the insertion apparatus comprises:
a control wire (30) rotatable about an elongate axis; and an engaging part (31) which is provided at the distal end of the control wire, and engages with the surgical tool,
the surgical tool is provided with a connection member (62) which is connected to the engaging part, and
the engaging part and connection member have plane parts (31c, 62j) to transmit a rotating force caused by the rotation of the control wire to the connection member from the engaging part.

What is claimed is:

1. An insertion apparatus for an endoscope, the apparatus comprising:
    a tubular body configured to be inserted into a surgical tool insertion channel of the endoscope; and
    a wire member configured to be inserted into an inside cavity of the tubular body,
    wherein the tubular body comprises:
    a distal end coil which is provided in the distal end side of the tubular body;
    a proximal end coil which is provided at the proximal end of the distal end coil, and has an inside diameter smaller than an inside diameter of the distal end coil; and
    an inside diameter changed member which is provided between the proximal end of the distal end coil and the distal end of the proximal end coil, and comprising a reducing inside diameter to connect the proximal end of the distal end coil and the distal end of the proximal end coil such that the reducing inside diameter progressively reduces from a proximal end side of the distal end coil to a distal end side of the proximal end coil,
    wherein the inside diameter changed member has a tapered-shape with the distal end side length L determined by a thickness value H and the bending radius R obtained by the insertion section configured to be bent to a maximum, and the thickness value H is obtained by subtracting the thickness of the distal end coil from the thickness of the proximal end coil.

2. The insertion apparatus for the endoscope according to claim 1, wherein the diameter of the distal end of the proximal end coil has a tapered-shape to reduce from a distal end side of the proximal end coil to a proximal end side of the proximal end coil.

3. An insertion apparatus for an endoscope, the apparatus comprising:
    a distal end coil;
    a proximal end coil which is provided at a proximal end of the distal end coil, and has an inside diameter smaller than an inside diameter of the distal end coil;
    a control wire which is provided movably in the distal end coil and proximal end coil;
    a surgical tool which is removably provided at a distal end of the control wire, and controlled by the control wire; and
    a connection member which is provided between the proximal end coil and distal end coil, and formed to have an inside diameter which gradually decreases from the distal end toward the proximal end,
    wherein the inside diameter of the connection member has a tapered-shape with the distal end side length L determined by a thickness value H and the bending radius R obtained by the insertion section configured to be bent to a maximum, and the thickness value H is obtained by subtracting the thickness of the distal end coil from the thickness of the proximal end coil.

4. The insertion apparatus for the endoscope according to claim 3, wherein the diameter of the distal end of the proximal end coil has a tapered-shape to reduce from a distal end side of the proximal end coil to a proximal end side of the proximal end coil.

5. The insertion apparatus for the endoscope according to claim 3, wherein the surgical tool is a clip unit with a clip configured to be left in tissue of a patient.

6. The insertion apparatus for the endoscope according to claim 3, wherein the surgical tool is grasping forceps configured to grasp tissue of a patient.

7. The insertion apparatus for the endoscope according to claim 3, wherein the surgical tool is a snare configured to bind tissue of a patient.

8. An insertion apparatus for an endoscope, the apparatus comprising:
    a tubular body configured to be inserted into a surgical tool insertion channel of the endoscope; and
    a wire member configured to be inserted into an inside cavity of the tubular body,
    wherein the tubular body comprises:
    a distal end coil which is provided in the distal end side of the tubular body;
    a proximal end coil which is provided at the proximal end of the distal end coil, and has an inside diameter smaller than an inside diameter of the distal end coil; and
    a connection member which is provided between the distal end coil and the proximal end coil, and connects the distal end coil and proximal end coil, and
    the connection member has an inside diameter that decreases gradually from the distal end side toward the proximal end side, to approximate the inside diameters of the proximal end of the distal end coil and the distal end of the proximal end coil,
    wherein the inside diameter of the connection member has a tapered-shape with the distal end side length L determined by a thickness value H and the bending radius R obtained by the insertion section configured to be bent to a maximum, and the thickness value H is obtained by subtracting the thickness of the distal end coil from the thickness of the proximal end coil.

9. The insertion apparatus for the endoscope according to claim 8, wherein the diameter of the distal end of the proximal end coil has a tapered-shape to reduce from a distal end side of the proximal end coil to a proximal end side of the proximal end coil.

10. An insertion apparatus for an endoscope comprising:
    a distal end coil;
    a proximal end coil which is provided at a proximal end of the distal end coil, and has an inside diameter smaller than an inside diameter of the distal end coil;
    a connection member which is provided between the proximal end coil and distal end coil, and connects the proximal end coil and distal end coil;
    a control wire which is provided movably in the distal end coil, connection member and proximal end coil; and
    a surgical tool which are provided removably at a distal end of the control wire, and controlled by the control wire;
    wherein an inside diameter of the connection member decreases gradually from the distal end toward the proximal end,
    and the inside diameter of the connection member has a tapered-shape with the distal end side length L determined by a thickness value H and the bending radius R obtained by the insertion section configured to be bent to a maximum, and the thickness value H is obtained by subtracting the thickness of the distal end coil from the thickness of the proximal end coil.

11. The insertion apparatus for the endoscope according to claim 10, wherein the diameter of the distal end of the proximal end coil has a tapered-shape to reduce from a distal end side of the proximal end coil to a proximal end side of the proximal end coil.

12. The insertion apparatus for the endoscope according to claim 10, wherein the surgical tool is a clip unit with a clip configured to be left in tissue of a patient.

13. The insertion apparatus for the endoscope according to claim 10, wherein the surgical tool is a grasping forceps configured to grasp tissue of a patient.

14. The insertion apparatus for the endoscope according to claim 10, wherein the surgical tool is a snare configured to bind tissue of a patient.

* * * * *